US007183396B2

(12) United States Patent
Gomes et al.

(10) Patent No.: US 7,183,396 B2
(45) Date of Patent: Feb. 27, 2007

(54) LINVIN, A NOVEL INHIBITOR OF APOPTOSIS PROTEIN

(76) Inventors: Bruce C Gomes, 1800 Concord Pike, Wilmington, DE (US) 19850-5437; Garrett M Kasof, 1800 Concord Pike, Wilmington, DE (US) 19850-5437; Judith C Prosser, 1800 Concord Pike, Wilmington, DE (US) 19850-5437

( * ) Notice: Subject to any disclaimer, the term of this patent is extended or adjusted under 35 U.S.C. 154(b) by 504 days.

(21) Appl. No.: 10/244,586

(22) Filed: Sep. 16, 2002

(65) Prior Publication Data

US 2003/0087319 A1    May 8, 2003

(51) Int. Cl.
    C07H 21/04       (2006.01)
(52) U.S. Cl. .................. 536/23.1; 435/325; 435/320.1; 530/350
(58) Field of Classification Search ................ 530/350; 536/23.1
    See application file for complete search history.

(56) References Cited

U.S. PATENT DOCUMENTS

| 4,861,710 | A | * | 8/1989 | Sobel et al. .................... 435/6 |
| 6,020,143 | A |   | 2/2000 | St. George-Hyslop et al. |
| 6,284,487 | B1 |   | 9/2001 | Stahl et al. |

FOREIGN PATENT DOCUMENTS

| WO | WO 96/35703 | 11/1996 |
| WO | WO 97/06182 | 2/1997 |
| WO | WO 97/17937 | 5/1997 |
| WO | WO 98/22131 | 5/1998 |
| WO | WO 00/08144 | 2/2000 |
| WO | WO 00/23589 | 4/2000 |

OTHER PUBLICATIONS

Bowie et al, Science, 1990, 247:1306-1310.*
Boehringer Mannheim Biochemicals Catalog, 1994, p. 93, cat #1034 731.*
Orkin et al, Report and Recommendations of the Panel to Assess the NIH investment in Research on Gene Therapy, 1995, p. 1-39.*
Marshall Science, 1995, 269:1050-1055.*
Culver et al, TIG, 1994, 10:174-178.*
Liston et al., "Genomic Characterization of the Mouse Inhibitor of Apoptosis Protein 1 and 2 Genes", Genomics, Dec. 15, 1997, pp. 495-503.
Rajcan-Separovic et al., "Assignment of Human Inhibitor of Apoptosis Protein (IAP) Genes xiap, hiap-1, and hiap-2 to Chromosomes Xq25 and 11q22-q23 by Fluorescence in Situ Hybridization", Genomics, 1996, vol. 37, No. 3, pp. 404-406.
Young et al., "Genomic organization and physical map of the human inhibitors of apoptosis: HIAP1 and HIAP2", Mammalian Genome, Jan. 1999, vol. 10, No. 1, pp. 44-48.
Ambrosini et al., "A novel anti-apoptosis gene, survivin, expressed in cancer and lymphoma", Nat. Med., Aug. 1997, pp. 917-921.

Duckett et al., "A conserved family of cellular genes related to the baculovirus iap gene and encoding apoptosis inhibitors"; EMBO Journal, 1996, pp. 2685-2689.
Liston et al., "Suppression of apoptosis in mammalian cells by NAIP and a related of IAP genes", Nature, Jan. 1996, pp. 349-353.
Rothe et al., "The TNFR2-TRAF Signaling Complex Contains Two Novel Proteins Related to Baculoviral Inhibitor of Apoptosis Proteins", Cell, Dec. 1995, pp. 1243-1252.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", Journal of Cell Biology, 1990, vol. 111, pp. 2129-2138.
Lazar et al., "Transforming Growth Factor α: Mutation of Aspartic Acid 47 and Leucine 48 Results in Different Biological Activities", Molecular and Cellular Biology, 1988, vol. 8, pp. 1247-1252.
Stehlik et al., "Cytokine Induced Expression of Porcine Inhibitor of Apoptosis Protein (iap) Family Member is Regulated by NF-κB", Biochem Biophys Res Commun, 1998, vol. 243, pp. 827-832 (abstract).
Accession No. U79142.
Accession No. L49432.
Uren et al., "Cloning and expression of apoptosis inhibitory protein homologs that function to inhibit apoptosis and/or bind tumor necrosis factor receptor-associated factors", PNAS, 1996, vol. 93, pp. 4974-4978.
Accession No. U37546.
Accession No. AAT61591.
Brinbaum et al., "An Apoptosis-Inhibiting Gene from a Nuclear Polyhedrosis Virus Encoding a Polypeptide with Cys/His Sequence Motifs", Journal of Virology, 1994, vol. 68, pp. 2521-2528 (abstract).
Accession No. L22564.
Accession No. Y17793.
Accession No. AAT14884.
Accession No. AAT65102.
Accession Umber AF007769.

* cited by examiner

Primary Examiner—Jeffrey Siew
Assistant Examiner—Laura Goddard
(74) Attorney, Agent, or Firm—Fish & Neave IP Group Ropes & Gray, LLP

(57) ABSTRACT

A novel isolated and purified human protein inhibitor of apoptosis, termed livin, is described. A cDNA sequence which encodes the native inhibitor of apoptosis (livin) is disclosed as well as the structural coding region and the amino acid residue sequence. Molecular sequences are provided for the design and synthesis of entities that modulate biological and/or pharmacological activity of the native biomolecule. Methods are provided which employ the sequences to identify compounds that modulate biological and/or pharmacological activity of the native biomolecule. Biologically-effective antisense molecules as well as dominant negative mutant versions of the livin protein which are suitable for therapeutic are also provided. The invention is also drawn toward the study, prevention, diagnosis, and treatment of pathophysiological disorders related to apoptosis.

7 Claims, 5 Drawing Sheets

LINVIN, A NOVEL INHIBITOR OF APOPTOSIS PROTEIN

CROSS-REFERENCE TO RELATED APPLICATIONS

Figure 1A:
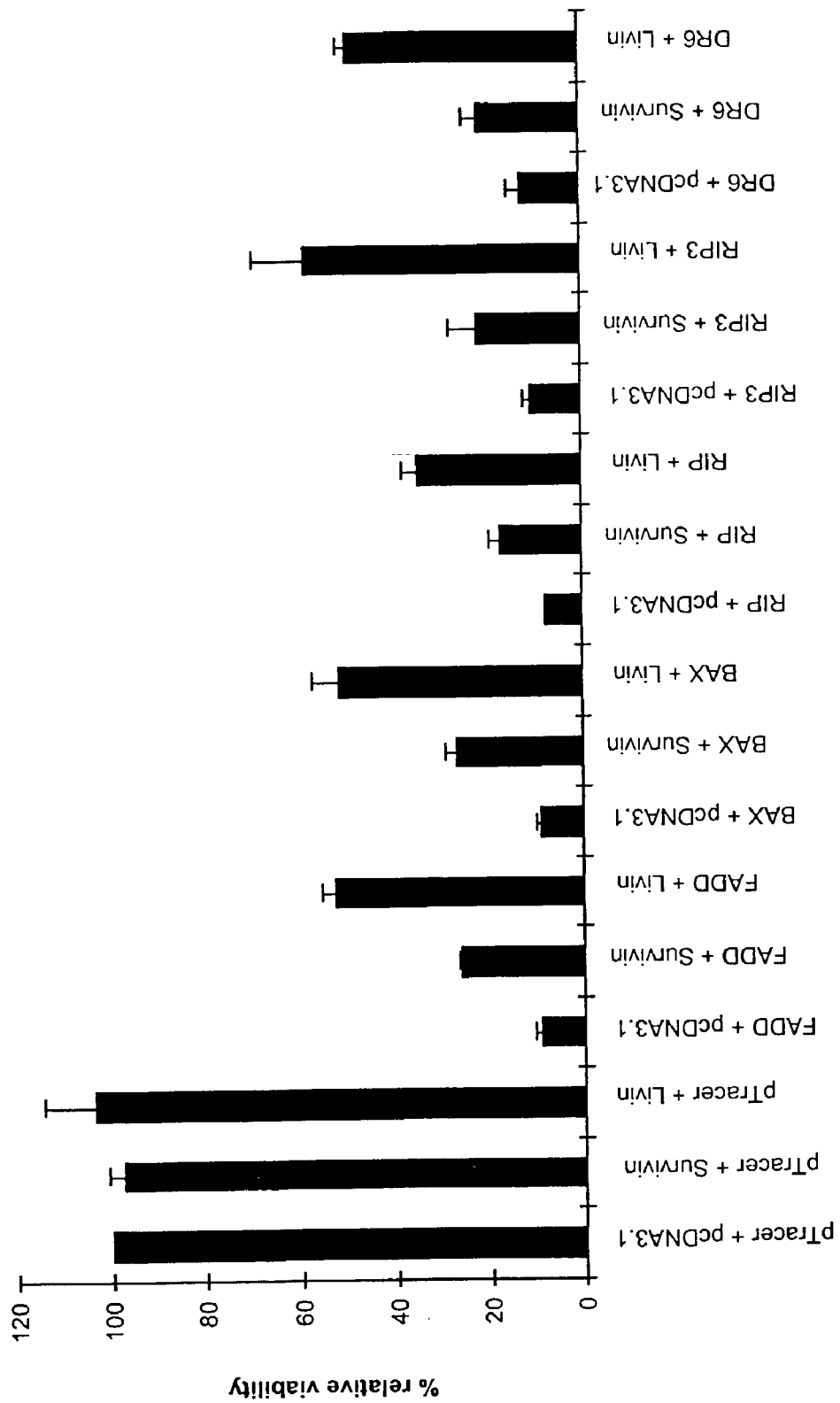

This application claims priority under 35 U.S.C. 120 to U.S. application Ser. No. 09/594,119, filed Jun. 14, 2000, now abandoned, which claims priority under 35 U.S.C. 119(e) to U.S. provisional application 60/139,291, filed Jun. 15, 1999, both of which are hereby incorporated by reference in their entirety.

SUMMARY

The present invention specifically relates to the identification of a novel human gene, which the inventors have termed livin (referred to as IAP-3 in the priority establishing application U.S. Ser. No. 60/139,291 filed 15 Jun. 1999), that encodes a protein that inhibits cellular apoptosis. Molecular sequences are provided for the design and synthesis of entities that modulate biological and/or pharmacological activity of the native biomolecule. The sequences are also provided for employment to identify compounds that modulate biological and/or pharmacological activity of the native biomolecule. Biologically-effective antisense molecules are provided, as well as dominant negative mutant versions of the livin protein which are suitable for therapeutic use. The invention is also drawn toward the study, prevention, diagnosis, and treatment of pathophysiological disorders related to apoptosis.

BACKGROUND TO THE INVENTION

The inhibitor-of-apoptosis protein (IAPs) family is characterized by one or more repeats of a highly conserved ~70 amino acid domain termed the baculoviral IAP repeat (BIR) and suppress apoptosis triggered by a wide variety of stimuli, including viral infection, chemotherapeutic drugs, staurosporin, growth factor withdrawal, and by components of the TNF-a/Fas apoptotic signaling pathways (Deveraux, Q. L. and Reed, J. C. (1999) *Genes & Dev.* 13:239–252; LaCasse et al., (1998) *Oncogene* 17:3247–3259; Miller, L. K. (1999) *Trends Cell Biol.* 9:323–328). While first identified in baculovirus, the AP family has been conserved evolutionarily from viruses to nematodes, flies, and several mammalian species. There are currently five human IAP family members, c-IAP1, c-IAP2, XIAP, NAIP, and survivin (Ambrosini, et al., (1997) *Nat. Med.* 3:917–921; Duckett et al., (1996) *EMBO J.* 15:2685–2689; Liston et al., (1996) *Nature* 379:349–353; Rothe et al., (1995) *Cell.* 83:1243–1252). Recombinant expression of IAP proteins blocks apoptosis induced by various stimuli (Duckett et al. ibid; Liston et al. ibid), and promotes abnormally prolonged cell survival in the developmentally-regulated model of the Drosophila eye, in vivo (Hay et al., (1995) *Cell.* 83:1253–1262). All of the human IAP family members, with the exception of NAIP, have been shown to interact with specific cysteine proteases, or caspases, required for the cleavage of certain proteins involved in the disassembly of the cell during apoptosis (Thomberry and Lazebnik (1998) *Science* 281:1312–1316). The caspases are synthesized as inactive zymogen forms which upon apoptotic stimulation are proteolytically processed in sequential manner into their active heterotetrameric forms. c-IAP1, c-IAP2, XIAP, and survivin bind potently to the active forms of the terminal caspases-3 and -7, but do not interact with caspases-8, which is the most proximal caspase from the TNF-a/Fas receptor (Deveraux et al., (1997) *Nature* 388:300–304; Roy et al., (1997) *EMBO J.* 16:6914–6925; Tamm et al., (1998) *Cancer Res.* 58:5315–5320). In addition, c-IAP1, c-IAP2, and XIAP bind to the zymogen form of caspase-9 thereby preventing its proteolytic processing as well as the processing of proteases, such as caspase-3, -6, and -7 (Deveraux et al., (1998) *EMBO J.* 17:2215–2223). Abrogation of caspase activity, a common downstream component of apoptosis, enables IAPs to have widespread anti-apoptotic potential.

The BIR domain forms a novel zinc-fold that is the critical motif for their anti-apoptotic activity and interaction with caspases (Hinds et al. (1999) *Nat. Struct. Biol.* 6: 648–651). While many IAPs contain up to three tandem BIR repeats, a single BIR domain is sufficient for caspase interaction and protection from apoptosis (Tamm et al., ibid; Takahashi et al., (1998) *J. Biol. Chem.* 273:7787–7790). Many of the IAP proteins (c-IAP1, c-IAP2, XIAP, as well as viral and insect IAPs) also contain a RING domain near their COOH-termini. The role for the RING domain varies depending on the AP and/or the apoptotic stimulus, but does not appear to be required for the anti-apoptotic activity of human IAPs (Roy et al., ibid; Takahashi et al. ibid; Hay et al., (1995) *Cell* 83:1253–1262; Vucic et al., (1998) *Mol. Cell. Biol.* 18:3300–3309). Deletion of the RING domain in c-IAP2 has suggested a critical role in TNF-a-mediated NF-kB activation, thereby providing an additional mechanism for the IAPs anti-apoptotic activity (Chu et al., (1997) *Proc. Natl. Acad. Sci.* 94:10057–10062). However, it is unclear if this is a general feature of the RING domain in other IAP family members.

Several of the IAP family members have been reported to play a role in pathological conditions, particularly neurodegenerative disorders and cancer. For instance, the NAIP gene was originally identified based on its deletion in patients with spinal muscular atrophy (SMA), a neurodegenerative disorder characterized by motor neuron depletion through apoptosis (Roy et al., (1995) *Cell* 80:167–178). The correlation between NAIP, SMA, and apoptosis suggests that NAIP may be required for the survival of these neurons and that mutations in the NAIP locus contribute to SMA. In addition, NAIP levels are transiently elevated following ischemia and damage can be inhibited by overexpression of NAIP in vivo (Xu et al., (1997) *Nature Med.* 3:997–1004). Other IAPs, particularly survivin, have been correlated with cancer. Survivin is overexpressed in nearly all human tumors and transformed cell lines, but is rarely present in normal adult tissues (Ambrosini et al. ibid; Tamm et al., ibid; Grossman et al., (1999) *Lab. Invest.* 79:1121–1126; Kawasaki et al., (1998) *Cancer Res.* 58:5071–5074; Lu et al., (1998) *Cancer Res.* 58:1808–1812; Saitoh et al., (1999) *Int. J. Oncol.* 15:137–141), and XIAP, c-IAP1, and c-IAP2 are expressed in malignant gliomas (Wagenknecht et al., (1998) *J. Biol. Chem.* 273:11177–11182). Depletion of survivin using antisense or dominant negative mutants induce apoptosis implying that survivin expression contributes to the survival of cancer cells (Grossman et al. ibid; Ambrosini et al., (1998) *J. Biol. Chem.* 273:11177–11182; Li, F et al., (1999) *Nature Cell Biol.* 1:461–466; Li, F et al.,(1998) *Nature* 396:580–584).

Abberantly increased apoptosis or abnormally prolonged cell survival may both contribute to the pathogenesis of human diseases, including autoimmune disorders, neurodegenerative processes, and cancer (Steller (1995) *Science* 267:1445–1449).

Therapeutic and diagnostic uses of nucleic acids that encode various inhibitors of apoptosis relating to a member of the IAP family have been described in the patent literature. See for example, International Patent Publication Nos. WO 97/06255, WO 97/26331, WO 97/32601 and WO 98/22589. WO 98/22589 (Yale University) describes and claims the survivin gene/protein.

The present invention derives from the identification of a further IAP gene and protein which the inventors have termed livin. The full-length cDNA isolated and sequenced (SEQ ID NO. 1) of the human livin gene is 1376 nucleotides in length. The coding sequence is 843 nucleotides in length (SEQ ID No. 2) and the corresponding protein sequence is 280 amino acids in length (SEQ ID NO. 3). The BIR domain is located from about amino acids 87–154 and the RING domain from about amino acids 249–258. The overall protein similarity of livin to other IAP family members based on the GAP pairwise sequence alignment (GCG®, Madison, Wis.) was 31.7% to c-IAP1, 31.1% to c-IAP2, 46.4% to XIAP, 30.3% to NAIP, and 32.8% to survivin. At a structural level it was similar to survivin with respect to having just a single BIR domain. However, livin does not have a coiled-coil domain like survivin, but rather contains a COOH-terminal RING domain found in c-IAP1, c-IAP2, and XIAP. Expression of livin inhibited apoptosis by a number of stimuli, whereas an antisense construct was shown to induce apoptosis. Like its other family members, livin was capable of binding to caspases that correlated with its anti-apoptotic activity. Restricted expression of livin mRNA during development and transformed cell lines suggests a very specific role for livin.

Since livin, described infra, is present in certain cancer cell lines and prevents apoptosis it appears to be a significantly valuable therapeutic target for cancers exhibiting reduced apoptosis, such as melanomas as well as tissues effected by elevated apoptosis (for example, neurodegenerative diseases like Alzheimer's or Parkinson's). Modulation of a biological and/or pharmacological activity of livin, as described herein, by means of small molecule therapeutic compounds or administration of a dominant negative mutant form, or antisense molecule, or therapeutic antibody is expected to ameliorate pathophysiological conditions associated with apoptosis.

BRIEF DESCRIPTIONS OF THE INVENTION

This invention is based, in part, on the isolation and identification of a novel protein that inhibits cellular apoptosis, herein referred to a livin. The invention therefore provides isolated livin protein, analogs, derivatives, variants and fragments thereof, nucleic acid molecules that encode all or part of the livin protein, antibodies (including polyclonal and monoclonal) that bind to livin, and antisense molecules base on the livin nucleic acid sequence.

The method further provides methods of expressing the livin protein in suitable host cells.

The invention further provides methods for identifying livin binding partners and methods for screening for compounds or molecules capable of blocking or modulating the association of livin with a binding partner.

The invention further extends to the therapeutic use of such compounds or molecules identified using the screening method and to the therapeutic use of the livin nucleic acids, antisense molecules, proteins and antibodies.

DETAILED DESCRIPTION OF THE INVENTION

According to a first aspect of the invention there is provided an isolated polypeptide comprising the amino acid sequence of SEQ ID No. 3, or a variant thereof, or a fragment of either of these sequences.

As used herein, a molecule of the invention, either nucleic acid (polynucleotide) or amino acid (polypeptide) sequence, is said to be isolated when it is substantially separated from contaminant nucleic acids or polypeptides which correspond to or are complementary to genes and proteins other than livin or fragments thereof. The isolated molecules can either by prepared synthetically, removed from their natural environment and isolated/separated from at least one other component with which they are naturally associated or, purified from a mixture of polynucleotides or polypeptides, such as when purified following recombinant expression of the polypeptide of interest by a host strain. The person skilled in the art can readily employ standard purification methodologies to obtain and isolate the livin molecules of the invention.

The present invention also relates to variants of nucleic acid sequences (e.g., SEQ ID NO:1 and SEQ ID NO:2) and amino acid sequences (e.g., SEQ ID NO:3) substantially as shown, which have changes, e.g., a polypeptide sequence comprising a sequence which differs from the sequence referred to by at least one amino acid substitution, preferably a conservative amino acid substitution, that demonstrate or perform substantially the same biological and/or pharmacological activity in substantially the same way, as well as molecules which comprise truncated versions of these variants. However, variant as used herein is intended to encompass all contemplated biologically effective dominant negative mutants.

As used herein, the term 'variant' includes naturally occurring allelic variants as well as non-naturally occurring variants, derivatives and analogs of the sequences depicted in SEQ ID NOs. 3. As used herein, a variant polypeptide is one which has in increasing order of preference, at least 80%, 85%, 90%, 95%, 96%, 97%, 98%, and 99% homology (interchangeably termed identity herein) to the sequence depicted in SEQ ID No. 3. Such variants will preferably retain some livin biological activity, i.e. the ability to inhibit cellular apoptosis.

A preferred variant, as depicted in SEQ ID NO:3 for instance, is one having at least 80% amino acid sequence homology (identity) to SEQ ID NO:3 or a biologically and/or pharmacologically active substantial fragment thereof. A more preferred variant is one having at least 90% amino acid sequence homology; an even more preferred variant is one having at least 95% amino acid sequence homology to the livin amino acid sequence as depicted in SEQ ID NO:3 or a biologically and/or pharmacologically active fragment thereof.

Thus, according to a further aspect of the invention there is provided an isolated polypeptide having at least 80% homology to the polypeptide whose amino acid sequence is depicted in SEQ ID No. 3, or a biologically and/or pharmacologically active fragment thereof.

Examples of variants include C- or N-truncated variants (such as DC86 and DN154 disclosed in Example I), deletion variants (such as deletion of the central BIR domain—amino acids, disclosed in Example III), substitution variants as well as addition and insertion variants. The term 'derivative' refers to a polypeptide encoded by a chemically modified livin gene, for example one wherein hydrogen has been replaced by an acyl or amino group, as well as polypeptides possessing one or more non-natural amino acids. When referring to a polypeptide or protein sequence, a functional variant is one that has retained at least some livin activity, i.e. ability to inhibit apoptosis. The variant polypeptides of the present invention may comprise internal, but preferably, terminal flanking sequences (fusion proteins) to facilitate protein purification. Such 'additional domain' sequences (FLAG sequences) may comprise for example, metal chelating peptides such as histidine-tryptophan modules (including 6-his tags) that allow purification on immobilised immunoglobulin, or peptide domains that allow purification on immobilised antibodies specific for the peptide. Other suitable 'additional purification domains' will be known to the person skilled in the art.

Polypeptide fragments, as used herein comprise at least 20 amino acids, preferably at least 30 amino acids and more preferably at least 50 amino acids. Such fragments may be used as intermediates to generate longer polypeptide fragments including preferably, the full-length polypeptide sequence as depicted in SEQ ID No. 3, or a functional variant thereof. Such polypeptide fragments may also be used to raise antibodies against parts of the livin protein (see Example II below).

As noted above, a variant of livin of the present invention, may have an amino acid sequence that is different by one or more amino acid substitutions to the sequence disclosed in SEQ ID NO:3. Embodiments which comprise amino acid deletions and/or additions are also contemplated. The variant may have conservative changes (amino acid similarity), wherein a substituted amino acid has similar structural or chemical properties, for example, the replacement of leucine with isoleucine. A variant may have nonconservative changes, e.g., replacement of a glycine with a tryptophan. Guidance in determining which and how many amino acid residues may be substituted, inserted or deleted without abolishing biological or proposed pharmacological activity may be reasonably inferred in view of this disclosure and may further be found using computer programs well known in the art, for example, DNAStar software.

Amino acid substitutions may be made, for instance, on the basis of similarity in polarity, charge, solubility, hydrophobicity, hydrophilicity, and/or the amphipathic nature of the residues as long as a biological and/or pharmacological activity of the native molecule is retained. However, amino acid substitutions are important to construct contemplated biologically effective dominant negative mutants, several species of which are set forth herein.

Negatively charged amino acids, for example, include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine. However, in the construction of biologically effective dominant negative mutants at least one amino acid residue position at an active site required for biological and/or pharmacological activity in the native peptide is changed to produce an agent or entity having reduced activity or which is devoid of detectable native wild type activity.

Suitable substitutions of amino acids include the use of a chemically derivatized residue in place of a non-derivatized residue. D-isomers as well as other known derivatives may also be substituted for the naturally occurring amino acids. See, e.g., U.S. Pat. No. 5,652,369, Amino Acid Derivatives, issued Jul. 29, 1997. Example substitutions are set forth in TABLE 1 as follows:

TABLE 1

| Original residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences are aligned so that the highest percentage homology (match) is obtained, after introducing gaps, if necessary, to achieve maximum percent homology. N- or C-terminal extensions shall not be construed as affecting homology. "Identity" per se has an art-recognized meaning and can be calculated using published techniques. Computer program methods to determine identity between two sequences, for example, include DNAStar software (DNAStar Inc., Madison, Wis.); the GCG program package (Devereux, J., et al., Nucleic Acids Research (1984) 12(1):387); BLASTP, BLASTN, FASTA (Atschul, S. F. et al., J. Molec Biol (1990) 215:403). Homology (identity) as defined herein is determined conventionally using the well known computer program, BESTFIT (Wisconsin Sequence Analysis Package, Version 8 for Unix, Genetics Computer Group, University Research Park, 575 Science Drive, Madison, Wis. 53711). When using BESTFIT or any other sequence alignment program (such as the Clustal algorithm from the MegAlign software (DNASTAR)) to determine whether a particular sequence is, for example, about 80% homologous to a reference sequence, according to the present invention, the parameters are set such that the percentage of identity is calculated over the full length of the reference nucleotide sequence or amino acid sequence and that gaps in homology of up to about 20% of the total number of nucleotides in the reference sequence are allowed. Eighty percent of homology is therefore determined, for example, using the BESTFIT program with parameters set such that the percentage of identity is calculated over the full length of the reference sequence, e.g., SEQ ID NO:3, and gaps of up to 20% of the total number of amino acids in the reference sequence are allowed, and wherein up to 20% of the amino acid residues in the reference sequence may be deleted or substituted with another amino acid, or a number of amino acids up to 20% of the total amino acid residues in the reference sequence may be inserted into the reference sequence. Percent homologies are likewise determined, for example, to identify preferred species, within the scope of the claims appended hereto, which reside within the range of about 80 percent to 100 percent homology to SEQ ID NO:3 as well as biologically and/or pharmacologically active functional derivatives thereof and biologically effective dominant negative mutants. As noted above, N- or C-terminal extensions shall not be construed as affecting homology. Thus, when comparing two sequences, the reference sequence is generally the shorter of the two sequences. This means that for example, if a sequence of 50 nucleotides in length with precise identity to a 50 nucleotide region within a 100 nucleotide polynucleotide is compared there is 100% homology as opposed to only 50% homology.

Although the natural polypeptide of SEQ ID NO. 3 and a variant polypeptide may only possess for example 80% identity, they are actually likely to possess a higher degree of similarity, depending on the number of dissimilar codons that are conservative changes. Conservative amino acids substitutions can frequently be made in a protein without altering either the conformation or function of the protein. Similarity between two sequences includes direct matches as well as conserved amino acid substitutes which possess similar structural or chemical properties, e.g. similar charge.

Percentage similarity (conservative substitutions) between two polypeptides may also be scored by comparing the amino acid sequences of the two polypeptides by using programs well known in the art, including the BESTFIT program, by employing default settings for determining similarity.

The livin polypeptides of the invention can be synthesised using standard peptide synthesis technology, such as the Merryfield technique (*J. Amer. Chem. Soc.* 85:2149–2154, 1968), or by chemical cleavage methods known to the person skilled in the art based on the amino acid sequence of the livin protein depicted in SEQ ID No. 3. Numerous automated polypeptide synthesisers, such as Applied Biosystems 431A Peptide Synthesizer also now exist. Alternatively, and preferably, the polypeptides of the invention are produced from a nucleotide sequence encoding the polypeptide using recombinant expression technology.

The livin polypeptides of the invention can be used to generate antibodies which will specifically react with that particular livin polypeptide/protein. In a preferred embodiment the antibody binds to the anti-apoptotic BIR domain between positions 87 and 154 of SEQ ID No. 3, and antagonises livin activity. Example II describes the preparation of a polyclonal antibody against a livin polypeptide region (positions 201–221 in SEQ ID No. 3=SEQ ID No. 5).

Thus according to another aspect of the invention there is provided an antibody that specifically binds to part of the livin protein. Anti-livin antibodies that are particularly contemplated are monoclonal or polyclonal antibodies as well as antibody fragments containing the antigen binding domain and/or one or more complementarity determining regions of these antibodies. As used herein, an antibody fragment is defined as at least a portion of the variable region of the immunoglobulin molecule which binds to its target, i.e. the antigen binding region.

Such antibodies have a number of uses which will be evident to the molecular biologist or immunologist of ordinary skill. For example, antibodies against livin can be used to detect the presence of livin polypeptides in a test sample, i.e. in diagnostic, prognostic or imaging methodologies; as therapeutic molecules to antagonise endogenous livin and treat diseases and tissues affected by altered apoptosis, such as cancers (particularly melanoma cancer), Alzheimer's disease and Parkinson's disease; and, in methods to purify livin polypeptides, for example by incubating an anti-livin antibody that has been coupled to a solid matrix with a solution containing the livin polypeptide under conditions which permit binding of the antibody to the livin polypeptide; washing the solid matrix to remove contaminating components from the solution; and, eluting the livin polypeptide from the coupled antibody-matrix. Other uses include, but are not limited to, monitoring enzyme expression and development of assays to measure enzyme activity. Enzyme linked immunosorbant assays (ELISAs) are well known in the art and would be particularly suitable for detecting the livin polypeptide or fragments thereof.

A suitable method for purifying livin polypeptide molecules of the invention would be to use livin antibody affinity columns made by adding the anti-livin antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing livin polypeptides using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. Purified livin polypeptide is then dialyzed against phosphate buffered saline/detergent.

Various methods for the preparation of antibodies are well known to the person skilled in the art. Polyclonal antibodies raised against the polypeptides of the invention may be obtained for example, by injecting the polypeptide(s) into a selected mammal (i.e. rabbit, mouse, goat or horse), and later collecting the immunised serum from the animal, and treating this according to procedures known in the art (see for example, "Antibodies: A Laboratory Manual", CSH Press, Eds, Harlow and Lae (1988)). Depending on the host species, various adjuvants may be used to enhance the immunological response against the injected polypeptide. Suitable adjuvants include, but are not limited to Freud's, aluminium hydroxide and SAF.

Monoclonal antibodies may be produced by hybridoma cells, phage display libraries or other methodology. Monoclonal antibodies may be inter alia, human, rat or mouse derived. For the production of human monoclonal antibodies, hybridoma cells may be prepared by fusing spleen cells from an immunised animal, e.g. a mouse, with a tumour cell. Appropriately secreting hybridoma cells may thereafter be selected (Koehler & Milstein. *Nature.* 256:495–497, 1975; Cole et al. "Monoclonal antibodies and Cancer Therapy, Alan R Liss Inc, New York N.Y. pp 77–96). Monoclonal antibodies can be produced in vivo by, for example, injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art. In vitro production of the anti-livin polypeptide mAb can be carried out by growing the hydridoma in DMEM containing about 2% fetal calf serum to obtain sufficient quantities of the specific mAb. The mAb can then be purified by techniques known in the art.

Rodent antibodies may be humanised using recombinant DNA technology according to techniques known in the art.

Alternatively, chimeric antibodies, single chain antibodies, Fab fragments may also be developed against the polypeptides of the invention (Huse et al. *Science.* 256:1275–1281, 1989), using skills known in the art.

Fully human livin monoclonal antibodies or fragments thereof may be generated using cloning techniques employing large immunoglobulin gene combinatorial libraries (i.e. phage display) (see for example, Griffiths and Hoogenboom, "Building an in vitro immune system: human antibodies from pahge display libraries." In: Protein Engineering of Antibody Molecules for Prophylactic and Therapeutic Applications in Man. Clark, M. (Ed.), Nottingham Academic, pp 45–64 (1993)).

The amino acid sequence of livin depicted in SEQ ID No. 3 may be used to select specific regions of the livin protein against which to prepare antibodies. Preferred regions are the BIR and RING domains located between amino acids 87–154 and 154–280 respectively.

Direct injection of nucleic acid into a host animal can also be used as an immunogen to raise antibodies.

The current invention is also drawn toward a diagnostic composition comprising an antibody for the identification of a polypeptide sequence comprising the amino acid sequence substantially as shown in SEQ ID NO:3 or a variant thereof.

Another aspect of the invention provides a kit for detecting the presence of livin in a sample, comprising an antibody that binds specifically to livin and reagents to detect the antibody-livin complex.

A variety of protocols for detecting and measuring the expression of the novel molecule as well as functional derivatives thereof, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Methods-a Laboratory Manual*, APS Press, St Paul Minn.; Maddox, D. E., et al., J. Exp. Med. 158:1211.

The antibodies or reactive fragments thereof of the invention may be labeled with a suitable detectable marker such as a radioisotope, a fluorescent compound, a bioluminescent compound, a chemiluminescent compound, a metal chelator, and enzyme, or other antibody label molecule using techniques known in the art.

A further aspect of the invention provides isolated polynucleotides (including genomic DNA, genomic RNA, cDNA and mRNA; double stranded as well as +ve (sense) and –ve (antisense) strands) which encode the polypeptides of the invention. Single stranded DNA molecules of all or part of the livin gene either +ve or –ve strand, find use inter alia, as hybridisation probes, PCR amplification primers or antisense molecules. The sense strand of the complete gene sequence of native livin is depicted in SEQ ID No. 2. It will be appreciated that a polynucleotide of the invention may comprise any of the degenerate codes for a particular amino acid, including the use of rare codons. Indeed, when producing the polypeptide by recombinant expression in heterologous host strains, it may be desirable to adopt the codon useage (preference) of the host organism (Murray. *N.A.R.* 17:477–508, 1989).

Thus, according to a further aspect of the invention there is provided an isolated and/or purified polynucleotide molecule comprising a nucleic acid sequence which encodes a polypeptide comprising the sequence as depicted in SEQ ID NO:3 or a variant thereof, or a fragment of either of these sequences.

According to another aspect of the invention there is provided an isolated polynucleotide sequence comprising the sequence selected from the group consisting of:
(i) the nucleotide sequence of SEQ ID No. 1 or 2;
(ii) a nucleotide sequence having at least 80% sequence homology to (i);
(iii) a fragment of (i) or (ii);
(iv) a polynucleotide sequence of at least 17 nucleotides in length capable of selectively hybridising to (i), (ii) or (iii);
(iv) a nucleotide sequence fully complementary to (i), (ii), (iii) or (iv). Isolated polynucleotides of the present invention include but are not limited to sequences comprising SEQ ID NO:1 and SEQ ID NO:2.

The terms nucleic acid sequence and polynucleotide sequence are used interchangeably herein.

Nucleic acid sequences having at least 80% sequence homology with SEQ ID No.1 or 2, are sequences that code for variant livin proteins. In addition to homology alignment analysis, such sequences can be determined using hybridisation assays under suitably controlled stringency conditions. The present invention therefore particularly relates to polynucleotides which hybridise to the livin polynucleotide sequence depicted in SEQ ID NO. 1 or 2, its complementary sequence, or fragment thereof, under stringent conditions. As used herein, stringent conditions are those conditions which enable sequences that possess at least 80%, preferably at least 90% and more preferably at least 95% sequence homology to hybridise together. Thus, nucleic acids which can hybridise to the nucleic acid of SEQ ID No. 1 or 2, or the complementary antisense strand thereof, include nucleic acids which have at least 80%, preferably at least 90%, more preferably at least 95%, still more preferably at least 98% sequence homology and most preferably 100% with the nucleic acid encoding the livin gene disclosed herein. As well as full-length gene sequences, smaller nucleic acid fragments for example oligonucleotide primers which can be used to amplify the livin gene using any of the well known amplification systems such as polymerase chain reaction (PCR), or fragments that can be used as diagnostic probes to identify corresponding nucleic acid sequences are also part of this invention.

The invention thus includes polynucleotides of shorter length than the fill length livin gene sequence depicted in SEQ ID No. 2, that are capable of specifically hybridising to the nucleic acid encoding the livin gene described herein. Such polynucleotides may be at least 10 nucleotides in length, preferably at least 15, more preferably at least 20 and most preferably at least 30 nucleotides in length and may be of any size up to and including the full length livin nucleotide sequence.

An example of a suitable hybridisation solution when a nucleic acid is immobilised on a nylon membrane and the probe nucleic acid is greater than 500 bases or base pairs is: 6×SSC (saline sodium citrate), 0.5% SDS (sodium dodecyl sulphate), 100 µg/ml denatured, sonicated salmon sperm DNA. The hybridisation being performed at 68° C. for at least 1 hour and the filters then washed at 68°C. in 1×SSC, or for higher stringency, 0.1×SSC/0.1% SDS.

An example of a suitable hybridisation solution when a nucleic acid is immobilised on a nylon membrane and the probe is an oligonucleotide of between 12 and 50 bases is: 3M trimethylammonium chloride (TMACl), 0.01M sodium phosphate (pH 6.8), 1 mM EDTA (pH 7.6), 0.5% SDS, 100 µg/ml denatured, sonicated salmon sperm DNA and 0.1 dried skimmed milk. The optimal hybridisation temperature (Tm) is usually chosen to be 5° C. below the Ti of the hybrid chain. Ti is the irreversible melting temperature of the hybrid formed between the probe and its target. If there are any mismatches between the probe and the target, the Tm will be lower. As a general guide, the recommended hybridisation temperature for 17-mers in 3M TMACl is 48–50° C.; for 19-mers, it is 55–57° C.; and for 20-mers, it is 58–66° C.

Although hybridisation analyses can be undertaken to determine whether or not a nucleic acid sequence has 80% or more homology with SEQ ID No. 1 or 2, or fragments thereof, it is preferred that nucleotide alignment analyses using suitable computer software as described herein, is used.

The polynucleotides of the invention are useful for a variety of purposes, including but not limited to their use as hybridisation probes for detecting livin nucleotide sequences in a test sample etc.; as primers for amplification of all or part of the livin gene; as reagents for the diagnosis or prognosis of diseases mediated by inappropriate apoptosis (i.e. cancer, Alzheimers' disease or Parkinson's disease); as coding sequences capable of directing the expression of livin polypeptide sequences; as tools for modulating the expression of the livin gene(s); as reagents in gene therapy; as tools for use in developing screening assays for identifying chemical modulators of livin (apoptosis inhibitory) activity; and as therapeutic agents i.e. antisense molecules.

The invention further comprises convenient fragments of any one of the above sequences. Convenient fragments may be defined by restriction endonuclease digests of nucleic acid comprising the livin gene sequence. Such fragments are useful inter alia, for expressing short polypeptides fragments of livin protein of the invention as well as for use as hybridisation probes. Thus, as well as full-length gene sequences, smaller nucleic acid fragments for example oligonucleotide primers which can be used to amplify the livin gene using any of the well known amplification systems such as linear primer extension or polymerase chain reaction (PCR), or fragments that can be used as diagnostic probes to identify corresponding nucleic acid sequences are also part of this invention. The invention thus includes polynucleotides of shorter length than the sequences depicted in SEQ ID No. 1 or 2, that are capable of specifically hybridising to said sequences Hybridisation probes can be short, chemically synthesised oligonucleotide probes approximately 10–50 nucleotides in length, or may be recombinantly expressed fragments of the livin gene of approximately 0.3–1.5 Kb in size. Single stranded oligonucleotide probes of approximately 20–40 nucleotides in length which are capable of specifically hybridising to and detecting livin gene sequences are preferred. The probe sequences need not be completely complementary to the target sequence but must, for example, be capable of specifically and selectively hybridising to the livin polynucleotide sequence in the test sample.

Following procedures well known in the art, the probes can be used to identify and isolate not only corresponding nucleic acid sequences (i.e livin gene sequences) but, if sufficiently homologous, can also be used to identify the analogous/corresponding gene from other organisms using techniques well known to the person skilled in the art. Such sequences may be comprised in libraries, such as genomic or cDNA libraries.

Primer sequences are generally between 15 and 45 nucleotides in length. If these sequences are double stranded they will have to be separated before use in amplification reactions. In a preferred embodiment the primers are single stranded oligonucleotide sequences.

The probe or primer sequences can be provided with a suitable detectable reporter molecule label such as a radio-isotope ($P^{32}$, tritium, $C^{14}$ or $S^{35}$), or a non-radioactive label such as digoxigenin or biotin, using techniques available to the person skilled in the art.

The present invention also provides RNA transcripts corresponding to any of the above livin sequences or fragments. RNA transcripts can be used to prepare a polypeptide of the invention by in vitro translation techniques according to known methods (Sambrook et al. "*Molecular Cloning—A Laboratory Manual, second edition* 1989"). The invention further comprises full-length or fragment lengths of livin gene (coding sequence) flanked by non-coding sequence which may include natural or non-natural sequence containing restriction enzyme recognition sequence motifs. The incorporation of suitable restriction enzyme recognition sites either side of the livin coding region, or indeed any polynucleotide sequence from livin, facilitates cloning of the livin gene or polynucleotide sequence into a suitable vector. A suitable polynucleotide comprises a full length livin gene (encoding the polypeptide that starts with methionine at position 1 and terminates with the serine that precedes the stop codon TAA at position 280 of SEQ ID No. 3) flanked by unique Kpn I (5'-end) and Apa I (3'-end) restriction sites. Nucleotide changes or mutations may be introduced into a polynucleotide sequence by de novo polynucleotide synthesis, by site directed mutagenesis using appropriately designed oligonucleotide primers or by any other convenient means know to the person skilled in the art.

For expression purposes, it may be advantageous to engineer a restriction site at the 5'-end which is also capable of reconstituting the native amino-terminal methionine of the protein. The cleavage recognition sequence for the Nco I restriction enzyme not only includes a sequence that codes for methionine, but also one that is capable of retaining a functional Kozak consensus sequence, enabling the livin gene to be cloned at the 3'-end of a suitable promoter element in an expression vector.

The DNA polynucleotides can be synthesised chemically, or isolated by one of several approaches known to the person skilled in the art such as polymerase chain reaction (PCR) or ligase chain reaction (LCR) or by cloning from a genomic or cDNA library.

Once isolated (including once synthesised), a variety of expression vector/host systems may be used to express livin coding sequences. These include, but are not limited to microorganisms such as bacteria expressed with plasmids, cosmids or bacteriophage; yeasts, such as *Saccharomyces cerevisiae* or *Pichia pastoris*, tranformed with expression vectors; insect cell systems transfected with baculovirus expression systems; plant cell systems transfected with plant virus expression systems, such as cauliflower mosaic virus; or mammalian cell systems (for example those transfected with adenoviral vectors); selection of the most appropriate system is a matter of choice.

Expression vectors usually include an origin of replication, a promoter, a translation initiation site, optionally a signal peptide, a polyadenylation site, and a transcription termination site. These vectors also usually contain one or more antibiotic resistance marker gene(s) for selection. As noted above, suitable expression vectors may be plasmids, cosmids or viruses such as phage or retroviruses. The coding sequence of the polypeptide is placed under the control of an appropriate promoter, control elements and transcription terminator so that the nucleic acid sequence encoding the polypeptide is transcribed into RNA in the host cell transformed or transfected by the expression vector construct. The coding sequence may or may not contain a signal peptide or leader sequence for secretion of the polypeptide out of the host cell. Expression and purification of the polypeptides of the invention can be easily performed using methods well known in the art (for example, as described in Sambrook et al. "*Molecular Cloning—A Laboratory Manual, second edition* 1989").

Expression vectors are described herein as nucleic acid sequences for the transcription of embodiments of the present invention. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the livin molecule as well as variants and derivatives contemplated herein. Commercially available mammalian expression vectors which are suitable for recombinant expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active livin. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual,* 127. Vectors such as the INVITROGEN, MaxBac™ Baculovirus expression system, insect cells, and protocols are also preferred which are commercially available. INVITROGEN, Carlsbad, Calif.

Host cells transformed with a nucleotide sequence which encodes the livin inhibitor of apoptosis of the present invention may be cultured under conditions suitable for the expression and recovery of the encoded protein from cell culture. Embodiments of the present invention are host cells transformed with a purified polynucleotide comprising a nucleic acid sequence to encode the polypeptide having the sequence as depicted in SEQ ID NO:3 or a contemplated variant thereof Cells of this type or preparations made from them may be used to screen for modulators of the biological and/or pharmacological activity of the native molecules SEQ ID NO:1, SEQ ID NO:2, and SEQ ID NO:3.

Eukaryotic recombinant host cells are especially preferred. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells to express livin and derivatives thereof via any one of a number of techniques including but not limited to transformation, transfection, lipofection, protoplast fusion, and electroporation.

Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of livin production. Identification of host cell clones which express livin may be performed by several means, including but not limited to immunological reactivity with antibodies described herein, and/or the presence of host cell-associated specific biological activity, and/or the ability to covalently cross-link specific substrate to the novel kinase with the bifunctional cross-linking reagent disuccinimidyl suberate or similar cross-linking reagents.

The livin polypeptide(s) of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., *Protein Exp. Purif.* (1992), 3:263) protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and the coding region is useful to facilitate purification.

Systems such as the CLONTECH, TALON™ nondenaturing protein purification kit for purifying 6× His-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, W138, NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express SEQ ID NO:2/SEQ ID NO:3, for example, may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Livin can be produced in the yeast *S. cerevisiae* following the insertion of the optimal cDNA cistron into expression vectors designed to direct the intracellular or extracellular expression of the heterologus protein. In the case of intracellular expression, vectors such as EMBLyex4 or the like are ligated to the beta subunit cistron. See, e.g., Rinas, U., et al., *Biotechnology*, 8:543 (1990); Horowitz, B., et al., *J. Biol. Chem.*, 265:4189 (1989). For extracellular expression, the kinase cistron is ligated into yeast expression vectors which may employ any of a series of well-characterized secretion signals. The levels of expressed novel kinase are determined by the assays, such as ELISA or RIA described herein. In addition to *S. cerevisiae, Pichia pastoris* is another example of a much used yeast host strain for heterologous protein expression.

Genes encoding livin can be turned off by transforming a cell or tissue with expression vectors which express high levels of a polynucleotide, or a fragment thereof, encoding livin. Such constructs may be used to introduce untranslatable sense or antisense sequences into a cell.

Nucleic acid sequences complementary to all or part of SEQ ID NO:1 and/or SEQ ID NO:2 are used in another embodiment of the invention to modulate activation of apoptosis by affecting gene expression, e.g., transcription and/or translation of the subject sequences, in cells. Pharmacological activity of an endogenous gene may be modulated by affecting the transcription and/or translation, for example, of the endogenous gene by use or administration of anti-sense constructs to produce anti-sense transcripts or by direct delivery of anti-sense oligomers. It is thus a further object of this invention to provide oligonucleotides and oligonucleotide analogs which are capable of hybridising with messenger RNA of livin to inhibit the function of the messenger RNA through antisense interaction.

Persons of ordinary skill in the art will understand that the mRNA identified by the open reading frames (ORFs) of the DNA from which they are transcribed include not only the information from the ORFs, but also associated ribonucleotides which form the 5' cap region, the 5' untranslated region (UTR) and the 3' UTR region and that antisense oligonucleotides may be used to target any of these regions.

Recent studies have suggested that antisense oligonucleotides directed towards the 5' regions of the mRNAs, preferably the cap region and the start codon, are most effective at inhibiting gene expression.

Oligonucleotide analog as used herein, refers to moieties which function similarly to oligonucleotides but which have non-naturally occurring portions. Thus, oligonucleotide analogs may have altered sugar moieties or inter-sugar linkages. Exemplary amongst these are the phosphorothioate and other sulphur containing species which are known in the art. Oligonucleotide analogs also include species which include at least some modified bases. Although antisense oligonucleotides can be of any length including the entire coding region of livin cloned in the antisense orientation (as taught in Example V, herein), preferred antisense oligonucleotides and oligonucleotide analogs in accordance with this aspect of the invention are from about 3–50 subunits, more preferably about 8–35 subunits and still more preferably about 12–25 subunits. A subunit being a base and sugar combination suitably bound to adjacent subunits by phosphodiester or other bonding.

Antisense constructs and oligomers may each be used as embodiments of the present invention and each are related to therapeutic method embodiments practiced via direct administration as defined herein. Translation is most effectively inhibited by blocking the mRNA at a site at or near the initiation codon. Thus, oligonucleotides complementary to the 5'-terminal region of the livin mRNA transcript are preferred. Other preferred embodiments are oligonucleotides which are complementary the regions of SEQ ID NO:1 and/or 5' region of SEQ ID NO:2 which are proximal to, or include, the translational start codon, or a portion thereof.

Antisense molecules which are complementary to a region within the SEQ ID NO:1 positions 469–670 are particularly preferred embodiments. As is the antisense complementary to the full-coding region from nucleotides 210–1053 of SEQ ID No.1.

Oligonucleotides which comprise sequences complementary to the following positions of SEQ ID NO: 1 are example embodiments of the invention: SEQ ID NO: 1 positions: 194–206; 195–207; 196–208; 197–209; 198–210; 199–211; 200–212; 201–213; 202–214; 203–215; 204–216; 205–217; 206–218; 207–219; 208–220; 209–221; 210–222; 211–223; 212–224; 213–225; 214–226; 216–228; 220–232; 225–237; 230–242; 240–252; 250–262; 270–282; 520–532; 525–537; 529–541; 530–542; 540–552; 555–567; 560–572; 570–582; 590–602; and 600–612. Larger antisense polynucleotides, for example up to about 100 nucleotides in length, are also envisaged.

Oligonucleotides which comprise sequences complementary to and hybridisable to the recited area of the livin mRNA are contemplated for therapeutic use. U.S. Pat. No. 5,639,595, *Identification of Novel Drugs and Reagents*, issued Jun. 17, 1997, wherein methods of identifying oligonucleotide sequences that display in vivo activity are thoroughly described, is herein incorporated by reference.

Nucleotide sequences that are complementary to the livin-encoding nucleic acid sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, *Hybrid Oligonucleotide Phosphorothioates*, issued Jul. 29, 1997, and U.S. Pat. No. 5,652,356, *Inverted Chimeric and Hybrid Oligonucleotides*, issued Jul. 29, 1997, which describe the synthesis and effect of physiologically-stable antisense molecules, are incorporated by reference. Antisense molecules may be introduced into cells by microinjection, liposome encapsulation or by expression from vectors harboring the antisense sequence. Antisense therapy may be particularly useful for the treatment of diseases where it is beneficial to reduce the biological and/or pharmacological activity of the inhibitor of apoptosis, livin.

Ribozymes, enzymatic RNA molecules, may also be used to catalyze the specific cleavage of RNA. The mechanism of ribozyme action involves sequence-specific hybridisation of the ribozyme molecule to complementary target RNA (i.e livin), followed by endonucleolytic cleavage. For example, engineered hammerhead motif ribozyme molecules may specifically and efficiently catalyze endonucleolytic cleavage of sequences encoding livin.

Specific ribozyme cleavage sites within any potential RNA target can initially be identified by scanning the RNA for specific ribozyme recognition cleavage motifs, including: GUA, GUU and GUC. Following this, short RNA sequences of about 18 ribonucleotides, corresponding to the region of the target gene containing the cleavage motif, may be tested for secondary structural features that might render the oligonucleotide inoperable. The suitability of candidate target motifs can also be evaluated by testing for accessibility to hybridisation with complementary oligonucleotides using ribonuclease protection assays.

Complementary ribonucleotide molecules and ribozymes of the invention (i.e. to livin) may be prepared by any method known in the art for synthesising nucleic acid molecules.

Embodiments of biological molecules which modulate apoptosis described herein, i.e., nucleic acids or dominant negative mutant versions thereof as well as antisense and ribozyme embodiments may be administered to a subject via gene therapy to modulate, i.e., boost or attenuate the corresponding biological and/or pharmacological activity or gene expression of an endogenous molecule which mediates apoptosis. Nucleic acid sequences of the present invention may be delivered ex vivo or in vivo to the cells of target organs in a tissue-specific manner. The livin coding region as well as variants thereof contemplated herein can be ligated into viral vectors which mediate transfer of the livin nucleic acid coding regions by infection of recipient host cells. Suitable viral vectors include retrovirus, adenovirus, adeno-associated virus, herpes virus, vaccinia virus, polio virus and the like. See, e.g., U.S. Pat. No. 5,624,820, *Episomal Expression Vector for Human Gene Therapy*, issued Apr. 29, 1997. GENOVO Corporation, for instance, Sharon Hill, Pa., at the date of this application, have a readily commercially available expression vector portfolio which comprise an assortment of vectors complete with well-established methods which consistently demonstrate tissue-specific expression and inducible tissue-specific expression. The GENOVO Corporation is an example source for vectors and methods to practice gene-therapy methods of the present invention. Nucleic acid coding regions of the present invention are incorporated into effective expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, DNA derived from SEQ ID NO:1, e.g., derivatives which encode dominant negative mutants or antisense molecules contemplated herein, can be transferred into cells for gene therapy by non-viral techniques including direct microinjection, receptor-mediated targeted DNA transfer using ligand-DNA conjugates or adenovirus-ligand-DNA conjugates, or lipofection membrane fusion. These procedures and variations thereof are suitable for ex vivo, as well as in vivo human signal-transduction kinase polypeptide gene therapy according to established methods in this art.

As disclosed above, the invention also provides methods for detecting or diagnosing livin polynucleotides or polypeptides, as well as methods for identifying a cell or cells which express livin. In particular, the invention provides assays for detecting or diagnosing livin polynucleotides or polypeptides in a biological sample, such as blood, plasma, serum, sputum, urine, stool, saliva, semen, bone marrow, cell preparations—including cell tissues such as skin, tumour mass, prostate, breast and other tissues, and the like. A number of methods for amplifying and/or detecting livin polynucleotides are known in the art and may be employed in the practise of this aspect of the invention, as are methods for detecting livin polypeptides. In one embodiment, a method for detecting livin mRNA in a sample comprises generating cDNA from the sample by reverse transcription using one or more primers; amplifying the cDNA so produced using sense and antisense oligonucleotides specific for PCR amplifying all or a part of the livin cDNA produced; and detecting the presence of the amplified livin cDNA. In another embodiment, the mRNA can be converted to cDNA with incorporation of a suitable label, such as a radioactively labelled dNTP, and the labelled cDNA so produced can be detected by hybridising to a complementary polynucleotide sequence which may for example be bound at a pre-defined position onto a substrate such as a glass, plastic, nylon or other type of membrane; and the label detected. In another embodiment, livin genomic DNA can be detected by using sense and antisense oligonucleotides specific for PCR amplifying all or a part of livin genomic DNA. Methods for detecting the presence of livin polypeptides in a tissue, cell or other biological sample are also well known and include, immunoprecipitation, immunohistochemical analysis, Western blot analysis, ELISA, ELIFA and the like. In one embodiment, a test sample potentially containing livin polypeptides can be contacted with polyclonal or monoclonal antibodies, or a labeled binding partner for the livin protein and binding to the livin polypeptide in the sample can be detected.

Determining the livin expression status, for example in cells of an individual, can be used to provide information useful for predicting susceptibility to particular diseases, disease stages and progression of diseases such as cancer (reduced apoptosis), Parkinson's disease and Alzheimer's disease (both elevated apoptosis).

Thus, according to a further aspect of the invention there is provided a method for detecting or diagnosing the presence of livin polypeptide or polynucleotide sequences in a test sample comprising contacting the test sample with an antibody, oligonucleotide probe, or oligonucleotide primer capable of specifically binding to a livin polypeptide or polynucleotide and determining whether livin is present in the sample on the basis of whether or not a binding compex is formed.

Livin, like the other IAPs, binds to binding partners such as the caspases. Accordingly, the invention further provides methods for isolating and identifying binding partners of livin. Specifically, a livin polypeptide of the invention can be used as capture probe to identify livin binding partners. As used herein, a livin binding partner is a biomolecule (such as a protein, DNA or other cofactor) that binds to livin and mediates livin inhibition of cellular apoptosis. For example, a livin polypeptide is mixed with an extract or fraction of a lysed cell that expressed livin under conditions that allow the association of a binding partner with livin. The entire livin polypeptide (as depicted in SEQ ID No. 3) can be used or a fragment, such as ΔN154 (see Example III) can be used. After association of the livin polypeptide with its binding partner, the livin/binding partner complex is separated from the mixture using standard techniques, such as, for example, immunoprecipitation using anti-livin antibodies or density/sedimentation centrifugation or chromatography. Alternatively, the livin polypeptide can be immobilised on a solid support, the binding partner allowed to associate, non bound materials washed away and the binding partner treated under appropriate conditions, such as mild alkali, to effect dissociation from livin. Alternatively, the well known yeast 2-hybrid system can be employed to identify livin binding partners using a livin polypeptide of the invention as bait. The yeast two-hybrid system uses the ability of a pair of interacting proteins to bring a transcription activation domain into close proximity with a DNA-binding site that regulates the expression of an adjacent reporter gene. Compounds which are able to modulate the biological activity of the novel biomolecule as defined herein are identified by the their ability to effect protein:protein interactions (reconstitution of the chimeric transcriptional activators) and hence the yeast 2-hybrid readout assays well-known to artisans of ordinary skill in this area of molecular biology. Fields, S., et al., Trends Genet., 10:286 (1994); Allen, J. B., et al., TIBS, 20:511 (1995). Fields, S., Song, O., Nature 340:245 (1989). Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Sternglanz, R., TIG, 10(8): 286 (1994); and U.S. Pat. No. 5,283,173, System to Detect Protein-Protein Interactions, and U.S. Pat. No. 5,468,614, which are incorporated herein by reference.

According to further aspects of the invention there are provided methods for screening for compounds or molecules capable of blocking or modulating the association of livin with a binding partner. Specifically the livin is mixed with a livin binding partner (such as caspase-3 or caspase-7 as well as cleaved or uncleaved caspase-9) in the presence and absence of an agent to be tested. After mixing under conditions that allow association of livin with its binding partner, the two reactions are analysed to determine whether or not the test agent affected the association of livin with its binding partner. Agents that block or reduce the association of livin with its binding partner will be identified as decreasing the amount of association in the reaction containing the test agent.

Thus according to a further aspect of the invention there is provided a method for identifying agents that block the interaction of livin with a livin binding partner comprising the steps of:

(i) incubating a livin polypeptide of the invention with a binding partner, or fragment thereof capable of binding to the livin polypeptide and an agent to be tested, and (ii) determining whether or not said agent blocks the binding of livin to said livin binding partner.

Further, the livin molecules of the present invention can be used in screening assays to identify antagonists or inhibitors which bind to, or interact with, livin, emulate its substrate, or otherwise inactivate the biomolecule or compete biologically, e.g., competitive interaction or competitive binding inhibition, with the native SEQ ID NO:3 biomolecule, variant or biologically active fragment thereof. The human livin inhibitor of apoptosis biomolecule, as well as derivatives contemplated herein are used in screening assays to identify agonists which agonize or mimic the biological and/or pharmacological activity, induce the production of or prolong the biological half-life of the molecule in vivo or in vitro.

Methods are provided to screen compounds individually, or libraries of compounds, for the identification of compounds which have the ability to modulate a biological and/or pharmacological activity of livin. The present invention is also directed to methods of screening for compounds which modulate the expression (transcription and/or translation) of DNA or RNA encoding livin. Compounds which modulate these activities may be DNA, RNA, peptides, proteins, or non-proteinaceous organic molecules (e.g., small molecule drug compounds).

Compounds may modulate an ultimate biological and/or pharmacological activity by increasing or attenuating the expression of DNA or RNA encoding the livin inhibitor of apoptosis or a function of the native SEQ ID NO:3. Compounds that modulate the expression of livin DNA or RNA or the function of the polypeptide may be detected by a variety of assays. The assay may be a simple "yes/no" assay to determine whether there is a change in expression or activity. The assay may be made quantitative by comparing the expression or function of a test sample with the levels of expression or function in a standard sample.

The livin inhibitor of apoptosis described herein, its functional fragments or oligopeptides can be used for screening therapeutic compounds in any of a variety of drug screening techniques. The fragment or entity employed in such a test may be free in solution, affixed to a solid support, borne on a cell surface, or located intracellularly. The abolition or modulation of activity or the formation of binding complexes, between the livin molecule and the agent being tested, may be measured, for example, by means provided. Accordingly, the present invention provides a method for screening a plurality of compounds for specific binding affinity with the native polypeptide SEQ ID NO:3 or a variant thereof contemplated herein, comprising providing a plurality of compounds; combining an embodiment of livin of the present invention with each of a plurality of compounds for a time sufficient to allow binding under suitable conditions; and detecting binding of an embodiment of the livin inhibitor of apoptosis, to each of the plurality of compounds, thereby identifying the compounds which specifically bind the livin polypeptide.

Methods of identifying compounds that modulate a biological and/or pharmacological activity of livin are generally preferred, which comprise combining a candidate compound modulator with a polypeptide comprising the sequence as depicted in SEQ ID NO:3 or a variant thereof contemplated herein, including an effective portion thereof, and measuring an effect of the candidate compound modulator on the biological and/or pharmacological activity of the polypeptide.

Alternatively, a candidate compound modulator can be combined with a host-cell expressing a polypeptide having the sequence as depicted in SEQ ID NO:3 or a variant thereof contemplated herein, or an effective portion thereof, and measuring an effect of the candidate compound modulator on the biological and/or pharmacological activity of the polypeptide or the host cell. Preferred cellular assays for modulators of livin fall into two general categories: 1) direct measurement of a biological activity, and 2) measurement of downstream events in the signaling cascade including cell/tissue/organism physiological manifestations.

Compounds which are identified generally according to methods described, contemplated, and referenced herein that modulate a biological and/or pharmacological activity of a protein which inhibits apoptosis, e.g., the sequence as depicted in SEQ ID NO:3, are especially preferred embodiments of the present invention.

According to a further aspect of the invention there is provided the use of a compound identified according to the methods described herein in the treatment of a dysfunctional apoptosis condition.

Cancers, particularly melanoma cancer, Alzheimer's disease and Parkinson's disease are examples of dysfunctional apoptosis conditions which the compounds and other therapeutic agents disclosed herein could treat.

According to a further aspect of the invention there is provided a method to treat cancer, particularly melanoma cancer, in a patient comprising the step of increasing the level of apoptosis in one or more cells of the cancer by decreasing the amount or activity of livin in said one or more cells. In a preferred embodiment this is undertaken by administering an agent that decreases the trasnscription or translation of livin mRNA in said one or more cancer cells, in an amount that is effective to increase the level of apoptosis in said one or more cells. In one embodiment this is performed by using an agent capable of blocking the interaction between livin and a livin binding partner.

According to a further aspect of the present invention there is provided a method for treatment of a patient in need of such treatment for a dysfunctional-apoptosis related condition which is mediated by livin, e.g., SEQ ID NO:3, comprising administration of a therapeutically effective amount of a modulating compound identified using sequences comprising sequences as depicted in SEQ ID NO:1 and/or SEQ ID NO:3 or a contemplated variant thereof as a pharmacological target in methods contemplated herein.

Thus, according to another aspect of the invention there is provided a compound identified using sequences comprising sequences as depicted in SEQ ID NO:1 and/or SEQ ID NO:3 or a contemplated variant thereof, or a pharmaceutically or veterinary acceptable salt or solvate thereof, for use in a method of treatment of the human or animal by therapy.

There is further provided use of a compound identified using the screening methods disclosed herein (i.e using sequences comprising sequences as depicted in SEQ ID NO:1 and/or SEQ ID NO:3 or a contemplated variant thereof or a pharmaceutically acceptable salt, prodrug or solvate thereof), in the manufacture of a medicament for the treatment of pathophysiological disorders related to apoptosis.

The invention also relates to pharmaceutical compositions which comprise molecules as depicted in SEQ ID NO:2 or SEQ ID NO:3 or variants of these molecules as defined herein for the treatment of pathological disorders related to or mediated by the livin.

Pharmaceutically and/or veterinary useful therapeutic compositions which comprise a derivative nucleic acid of SEQ ID NO:1, a dominant negative mutant coding region, an antisense molecule, a polypeptide as depicted in SEQ ID NO:3 or a variant thereof contemplated herein, or an antibody raised against such a polypeptide, or a compound identified by means encompassed by the claims appended hereto that modulates the biological and/or pharmacological activity a protein which inhibits apoptosis, e.g., SEQ ID NO:3, may be formulated according to known methods such as by the admixture of one or more pharmaceutically or veterinary acceptable excipients or carriers. Examples of such excipients, carriers and methods of formulation may be found in *Remington's Pharmaceutical Sciences* (Maack Publishing Co, Easton, Pa.). To form a pharmaceutically or veterinary acceptable composition suitable for effective administration, such compositions will contain an effective amount of a polypeptide, nucleic acid, antibody or compound modulator.

Therapeutic or diagnostic compositions of the invention are administered to an individual (mammal—human or animal) or used in amounts sufficient to treat or diagnose apoptosis-related disorders. The effective amount may vary according to a variety of factors such as the individual's condition, weight, sex and age. Other factors include the mode of administration.

The term functional derivative includes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

Pharmaceutical and veterinary compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans and other animals. A therapeutically effective dose refers to that amount of compound, peptide, antibody or nucleic acid which ameliorate or prevent a dysfunctional apoptotic condition. The exact dosage is chosen by the individual physician in view of the patient to be treated.

Compounds identified according to the methods disclosed herein as well as, therapeutic antibodies, therapeutic nucleic acids and peptides contemplated herein may be used alone at appropriate dosages defined by routine testing in order to obtain optimal modulation of livin activity. In addition, co-administration or sequential administration of these and other agents may be desirable.

The pharmaceutical or veterinary compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of a protein which mediates apoptosis can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound, nucleic acid, or peptide desired can be employed as an apoptosis modulating agent.

The daily dosage of the products may be varied over a wide range from 0.001 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of livin modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

Thus, according to another aspect of the invention there is provided, a pharmaceutical or veterinary acceptable composition comprising a compound identified using the screening methods disclosed herein, a polynucleotide of the invention, an antisense molecule derived from SEQ ID NO:1, or an antibody specific for the polypeptide depicted in SEQ ID No. 3, together with a pharmaceutically or veterinary acceptable excipient or carrier.

The invention will be further described by reference to the following non-limiting figures and examples:

FIG. 1. Livin suppresses apoptosis by multiple stimuli. (A) HeLa cells ($2\times10^5$) were co-transfected with 1 µg of pTracer-SV40 derived plasmids containing the apoptotic genes (DR6, FADD, RIP, RIP3, and Bax) along with 1 µg of pcDNA3.1-myc-survivin, pcDNA3.1/V5/His-TOPO-livin, or empty pcDNA3.1 vector. (B) HeLa cells were co-transfected with 1 µg of pTracer-SV40-RIP3, or empty pTracer-SV40 vector, and 1 µg of pcDNA3.1/myc-His-livin-DN154, -DC86, and -86–154, or empty pcDNA3.1 vector. Twenty-four hours post-transfection GFP levels were measured by laser scanning cytometry. At least 5000 cells were analyzed for each transfection. The graphs indicate relative viability which was calculated based on the percent of GFP-positive cells as compared to the control, empty pTracer-SV-40 with pcDNA3.1. Error bars represent standard error of the mean, N=3.

FIG. 2. Induction of apoptosis by livin antisense. (A) HeLa, G361, and SW480 cells were co-transfected with 0.5 µg of the pTracer-SV-40 marker plasmid along with 1.5 µg pcDNA3.1/N5/His-TOPO-livin (sense or antisense). GFP levels were measured by laser scanning cytometry 48 hours post-transfection. At least 5000 cells were analyzed for each transfection. The graph indicates relative viability which was calculated based on the percent of GFP-positive cells as compared to the control, empty pTracer-SV-40 with pcDNA3.1. Error bars represent standard error of the mean, N=3. (B) G361 cells were transfected with 1.5 µg of pcDNA3.1/V5/His-TOPO-livin antisense, or control pcDNA3.1 vector. Cells were harvested 24 hours post-transfection and DNA strand breaks were measured in situ using the TUNEL procedure with FITC-labeled dUTP. The percent of TUNEL-positive cells were assessed by laser scanning cytometry. At least 2000 cells were counted for each sample. Error bars indicate standard error of the mean, N=3. (C) HeLa cells were transfected with 1.5 µg of pcDNA3.1/V5/His-TOPO-livin (sense or antisense), or control pcDNA3.1 vector. DEVD-AFC hydrolysis was measured in cytosolic extracts prepared 24 hours post-transfection. AFC levels were monitored over a 1 hour period at 37° C. and recorded in relative fluorescence units (RFU). Error bars indicate standard error of the mean, N=3.

EXAMPLES

Example 1

Cloning of Livin Gene

A partial cDNA sequence of livin was identified in the proprietary Incyte LifeSeq database (accession number 1419118). To obtain the full-length construct an adult kidney cDNA library (Life Technologies, Grand Island, N.Y.) was screened with a livin-specific probe, 5'-CCTTCTAT-GACTGGCCGCTGA-3' (SEQ ID No. 4), using the GeneTrapper® cDNA positive selection system (Life Technologies, Grand Island, N.Y.). A low abundant clone was found which contained an in-frame stop codon in the 5'-untranslated region, suggesting it was a full-length gene. This gene, which we termed livin, was 1376 base pairs and predicted to encode a 280 amino acid protein. The coding sequence of livin was PCR cloned into pcDNA3.1/V5/His-TOPO (Invitrogen, Carlsbad, Calif.) in both the sense and antisense orientations. Deletion mutants of livin (DN154, DC86, and 86–154) were generated by PCR (using primer pairs corresponding to SEQ ID Nos 5 & 6, 7 & 8 and 9 & 10, respectively) and subcloned into the Kpn I/Apa I sites within pcDNA3.1/myc-His (Invitrogen, Carlsbad, Calif.). FADD (Genbank accession no. U24231), Bax (Genbank accession no. U22473), and DR6 (Genbank accession no. NM014452), were subcloned by PCR using primers designed from the sequences disclosed in said Genbank accession Nos, and ligated into pTracer-SV40 at EcoR I,/Not I, EcoR V/Not I, and Not I/Spe I sites, respectively. The pTracer-SV40-RIP plasmid was prepared by PCR from pMH-RIP (human RIP gene cloned into pMH (Boehringer Mannheim)) and ligated into the Kpn I/Not I sites in pTracer-SV40. The pTracer-SV40-RIP3 vector has human RIP3 (PCR cloned from a human monocyte cDNA library (Clontech)) cloned into EcoR V/Not 1 sites in pTracer SV-40. The pZeoSV2-Bcl-$x_L$ construct has human bcl-$x_L$ cloned into the mammalian expression vector pZeoSV2 (Invitrogen). The pcDNA3.1-myc-survivin construct, which has the myc and survivin epitopes PCR cloned into pcDNA3.1 (Invitrogen), was provided by Dr. Neil Hewitt (AstraZenenca Pharmaceuticals, Macclesfield, Cheshire, UK). The nucleotide sequences of all of the clones were confirmed by fluorescent terminator cycle sequencing using an automated 377 DNA sequencer (Perkin-Elmer, Applied Biosystems, Foster City, Calif.).

Example II

Preparation of Livin Antibody and Confirmation of Protein Expression

Antibodies against livin were generated to confirm protein expression. Antibodies against livin were prepared by Sigma Genosys (The Woodlands, Tex.). The synthetic peptide LPTPRREVQSESAQEPGARDV (SEQ ID No. 11) corresponding to amino acids 201–221 of livin was conjugated to keyhole limpet hemacyanin (KLH) and used as an immunogen in rabbits. The antisera was then affinity purified using the same peptide.

Cell lysates were prepared in G361 cells and immunoprecipitated with either the livin antibody or with a control antibody against myc. The samples were probed by western blot using the livin antibody. Two bands specific for livin were detected at ~42- and 90-kDa. The 42 kDa was slightly higher than the predicated molecular weight of livin and also ran slower than recombinant livin purified from bacteria. It is likely that this disparity is due to post-translational modifications that occur in mammalian cells. The nature of the 90 kDa protein is still unknown but may be a product of one of the other transcripts observed on the northern blot. Nevertheless, these results clearly show that livin protein is expressed in the melanoma cell line G361.

Example III

Anti-apoplotic Activity of Livin

While the BIR motif can confer an anti-apoptotic signal via caspase interactions, some BIR motifs are not as effective at suppressing apoptosis, and there are BIR-containing proteins with no apparent anti-apoptotic function (Takahashi et al., ibid; Vucic et al., ibid; Hauser et al., (1998) *J. Cell Biol.* 141:1415–1422). Therefore, not all BIR domain-containing proteins may be defined properly as an IAP. The potential anti-apoptotic activity of livin was investigated with respect to several pro-apoptotic signals, including DR6, FADD, RIP, RIP3, and Bax. These proteins act at different points within the apoptotic process. DR6 is a member of the TNF receptor family and thus is at the most upstream level of the apoptotic process (Pan et al., (1998) *FEBS Lett.* 451:351–356). FADD (Chinnaiyan et al., (1995) *Cell* 81:505–512), RIP (Stanger et al., (1995) *Cell* 81:513–523), and RIP3 (Sun et al., (1999) *J. Biol. Chem.* 274:16871–16875; Yu et al., (1999) *Curr. Biol.* 9:539–542) all act as adapter proteins within the TNF-a/Fas pathway. Bax is a potent inducer of apoptosis but may not have a direct role in TNF-a/Fas pathway (Oltvai et al., (1993) *Cell* 74:609–619). HeLa cells were transfected with these apoptotic genes in the pTracer vector containing the GFP marker for accessing viability. Transfection with any of the pro-apoptotic genes led to roughly a 90% reduction in viability, as compared to empty pTracer vector (FIG. 1A). Co-transfection of the apoptotic genes with either livin or survivin provided a 4–6-fold increase in viability. In general, the anti-apoptotic activity of livin appeared to be slightly more robust than survivin. In fact, survivin has been shown previously to be less effective at inhibiting apoptosis that other IAP family members (Tamm et al., ibid). These results clearly demonstrate that livin is a novel member of the IAP family capable of inhibiting apoptosis by several stimuli.

Figure 1B:
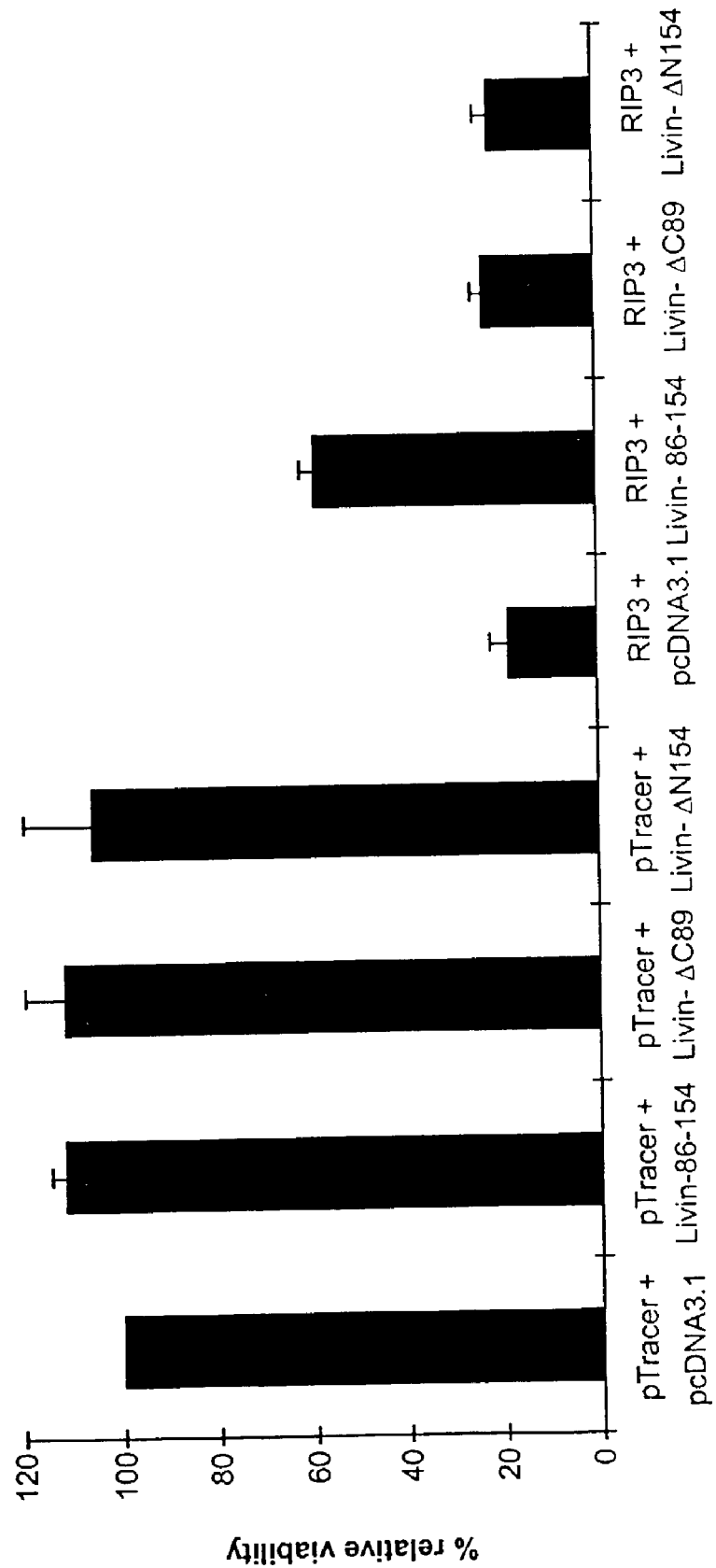

To determine the regions of livin necessary for its anti-apoptotic activity, three deletion mutants comprising either the NH$_2$-terminal (DC86; amino acids 1–86), the central BIR domain (86–154; amino acids 86–154), or the COOH-terminal RING domain (DN154; amino acids 154–280) were tested for their ability to block RIP3-mediated apoptosis. While the BIR domain is the critical region for anti-apoptotic activity within the IAP family, there may be some variations depending on the particular IAP and/or apoptotic stimulus. For example, a single BIR domain from c-IAP1, c-IAP2, or XIAP is sufficient for inhibiting caspase activity and etoposide-mediated apoptosis (Roy et al., (1997) ibid; Takahashi et al., ibid), whereas the BIR domain from survivin is not sufficient for inhibiting Taxol-induced apoptosis (Li et al., (1998) ibid). In addition, the baculoviral IAPs require both the BIR domain and the RING domain for their anti-apoptotic activity (Vucic et al., ibid). Site directed mutagenesis of XIAP revealed that actually the region adjacent to the BIR domain may play an important role in its activity (Sun et al., (1999) *Nature* 401:818–822). Here, it was found that the BIR domain of livin was sufficient for inhibiting RIP3-mediated apoptosis, and was nearly as effective as the wild-type protein (FIG. 1B). The NH$_2$- and COOH-terminal fragments could be detected by immunofluorescence but had no effect on apoptosis triggered by RIP3. Thus, the BIR domain of livin appears to be the critical motif involved in blocking apoptosis.

Maintenance of Cell Lines

HeLa, G361, SK-Mel29, HMCB, A375, WM115, HT144, and SW480 cell lines (ATCC, Rockville, Md.) were cultured in Dulbecco's Modified Eagle Medium (D-MEM) supplemented with 10% fetal bovine serum (FBS) and penicillin (100 U/ml)/streptomycin (0.1 mg/ml). The cells were maintained at 37° C./5% CO$_2$. Transfections were performed using LipofectAMINE Plus (Life Technologies, Grand Island, N.Y.) according to the manufacturer's specifications.

GFP Viability Assays

Viability was assessed using the green fluorescent protein (GFP) marker produced from pTracer-SV40-derived vectors. Transfected cells were fixed with 2% paraformaldehyde in PBS, counterstained with 10 µg/ml propidium iodide, 200 µg/ml RNase A, and 0.1% Tween-20 for 30 min at room temperature, and then mounted on microscope slides with Immu-mount (Shandon, Pittsburgh, Pa.). A laser scanning cytometer (LSC; CompuCyte, Cambridge, Mass.) was used to determine the percent of GFP-positive cells. The propidium iodide staining served as a marker required for gating the cell population. Relative fluorescence values were determined with an excitation at 488 nm using an argon laser and emission filters at 505–540 nm (GFP) and 614–639 nm (propidium iodide).

Example IV

Determining the Tissue Distribution of Livin.

The tissue distribution of livin was studied by Northern blotting with mRNA prepared from human adult and developmental tissues as well as several cancer cell lines. Using the entire cDNA sequence of livin as a probe, three distinct mRNAs were detected with approximate sizes of 1.4, 2.0, and 2.8 kB. The sizes of the three transcripts were distinct from other IAP family members, suggesting that they are specific for livin. Despite the presence of livin in fetal and adult kidney cDNA libraries, within the normal tissues tested here, livin was found only in placenta and fetal brain. It is likely that livin is expressed transcriptionally in other tissues, but at levels too low to be detected by the Northern blot. Elevated levels of livin were seen in cancer cell lines, particularly in the melanoma cell lines G361 and SK-Mel29, and to a lesser extent, in HeLa. While livin has a narrower distribution than survivin in cancer cells, the general patterns of expression between these genes are similar, with no detectable expression in normal adult tissues and elevated levels in placenta, developing tissues, and cancer cell lines (Ambrosini et al., ibid; Tamm et al., ibid).

Isolation of RNA and Northern Blotting

Poly(A)-RNA was isolated from human melanoma cell lines (SK-Mel29, HMCB, A375, WM115, and HT144) using the Poly(A) Pure kit (Ambion, Austin, Tex.) according to the manufacturer's specifications. The RNA was denatured in sample buffer [2.2 M formaldehyde, 50% formamide, 50 mM MOPS (pH 7.0), and 1 mM EDTA] heated at 65° C. for 10 min, electrophoresed in a 1% agarose gel containing 2.2 M formaldehyde, 50 mM MOPS (pH 7.0), and 1 mM EDTA, and then transferred by capillary elution onto HybondN™ nylon filters (Amersham Pharmacia Biotech, Piscataway, N.J.). In addition, commercially available human RNA blots, prepared from adult and fetal tissues and cancer cell lines (Clontech, Palo Alto, Calif.) were used. The blots were hybridized to random primed radiolabeled livin (full-length cDNA containing 5'- and 3'-UTR) or actin (Clontech, Palo Alto, Calif.) incubated in Hybrisol I™ (Oncor, Gaithersburg, Md.) overnight at 42° C. The blots were then washed with 2×SSC+0.05% SDS at room temperature followed by high stringency washing, 0.1×SSC+ 0.1% SDS at 50° C., and visualized using a PhosphorImager™ (Molecular Dynamics, Sunnyvale, Calif.).

Example V

Antisense to Livin Induces Apoptosis

The ability of antisense against livin to induce apoptosis was examined using TdT-mediated dUTP-X nick end labeling (TUNEL). Transiently transfected cells were stained with FITC-conjugated dUTP according to the manufacturer's specifications (Boehringer Mannheim, Indianapolis, Ind.). The cells were then counterstained with 10 μg/ml propidium iodide and 200 μg/ml RNase A, and collected on microscope slides by a cytospin. The percent of TUNEL-positive cells was evaluated using the LSC as described above for GFP.

Western blots were performed to confirm that the antisense construct of livin could reduce livin expression, but not survivin. Transfected HeLa cells were maintained in 100 μM ZVAD-fmk (Enzyme Systems, Livermore, Calif.) to prevent apoptosis. Cell lysates were prepared in Laemmli buffer and western blots were performed as described above using antibodies against V5 (Invitrogen) survivin (R & D Systems, Minneapolis, Minn.), and glyceraldehyde-3-phosphate dehydrogenase (Chemicon International, Inc., Temecula, Calif.).

An antisense construct was designed to include the entire coding region of livin cloned in the antisense orientation. There was no open reading frame in the antisense orientation of livin and therefore the construct did not result in the expression of new proteins. To verify that the antisense-construct could-reduce livin expression, we compared the levels of over-expressed livin protein in cells transfected with antisense to that of a control vector. To prevent apoptosis the cells were maintained in the presence of the general caspase inhibitor ZVAD-fmk.

HeLa cells or G361 cells (@2×10$^5$) were co-transfected with 1.5 μg of pcDNA3.1/N5/His-TOPO-livin antisense, or control pcDNA3.1 vector, with 0.5 μg of pcDNA3.1/V5/His-TOPO-livin, pcDNA3.1-myc-survivin, or control. Cells were maintained in 100 μM ZVAD-fmk to prevent apoptosis. Cell lysates were prepared 24 hours post-transfection and probed with monoclonal antibodies against the V5 epitope (livin), survivin, and GAPDH (control) and visualized by ECL.

In both HeLa and G361 cells, transfection with the antisense construct abrogated the expression of livin seen with the V5 antibody. In contrast, the antisense did not reduce the levels of survivin, suggesting that the construct has a specific effect on livin, and not on related IAP family members.

Figure 2A:
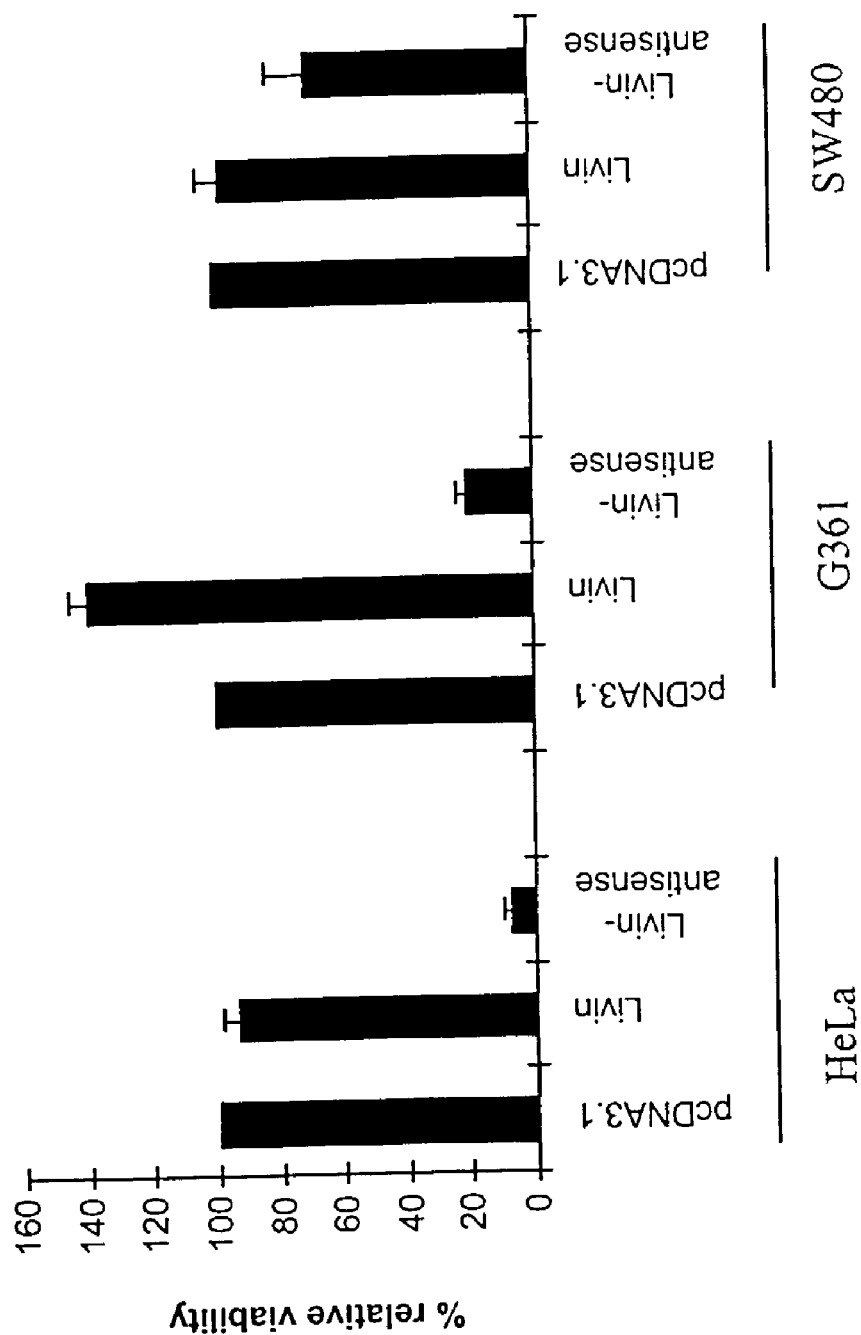

The effect of the antisense construct on cell viability was analyzed by co-transfection with an empty pTracer vector producing the GFP marker. Transfections were performed in HeLa and G361 cells, which normally express livin, as well as SW480 cells, which do not have detectable levels of livin mRNA. In HeLa or G361 cells the antisense decreased the percent of GFP-positive cells by 80–90% relative to the vector and sense controls (FIG. 2A). In contrast, transfection of the antisense into SW480 had little effect on GFP levels (FIG. 2A). These results demonstrate an effect of livin antisense on viability which correlated with livin expression.

Figure 2B:
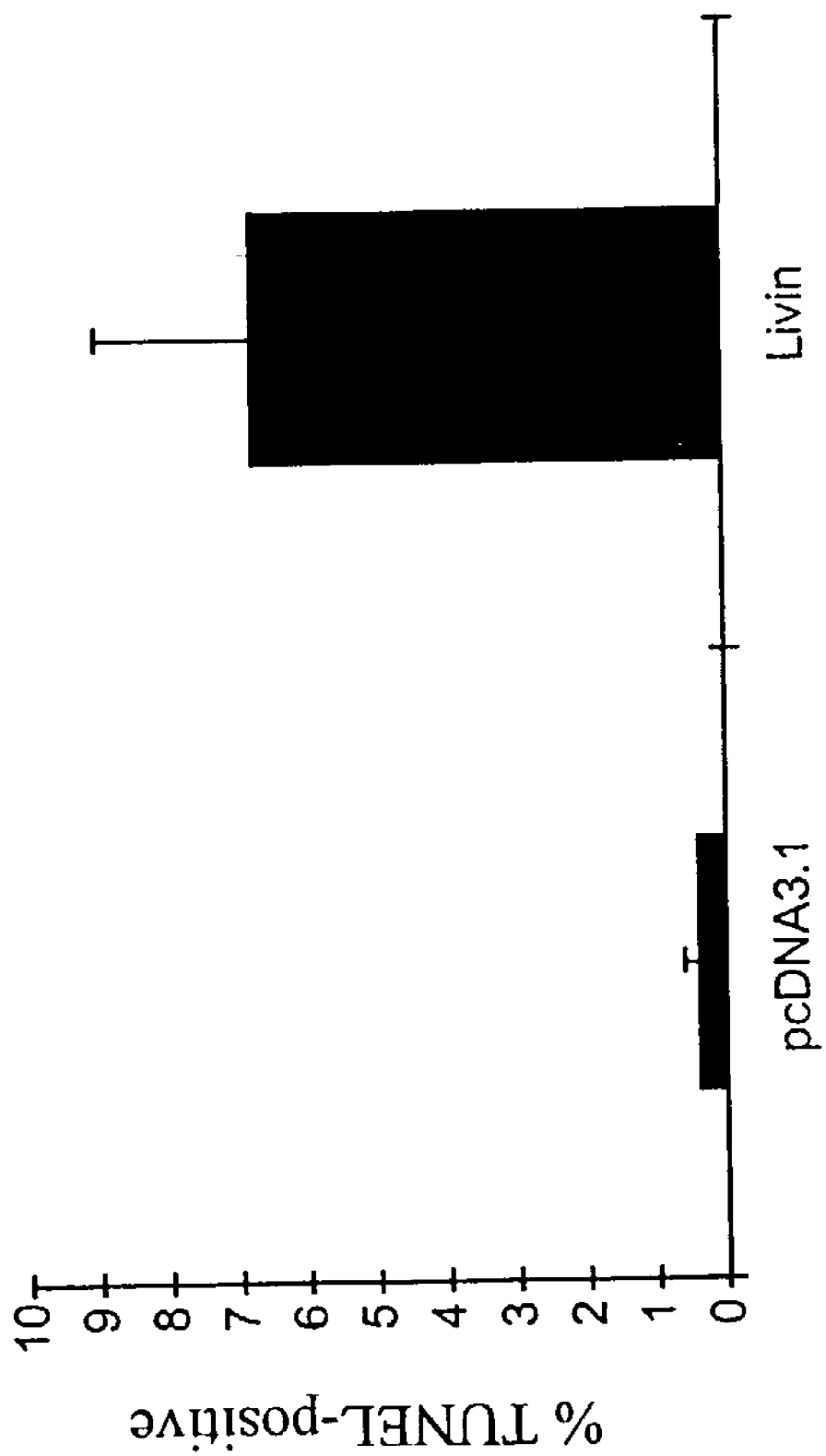
Figure 2C:
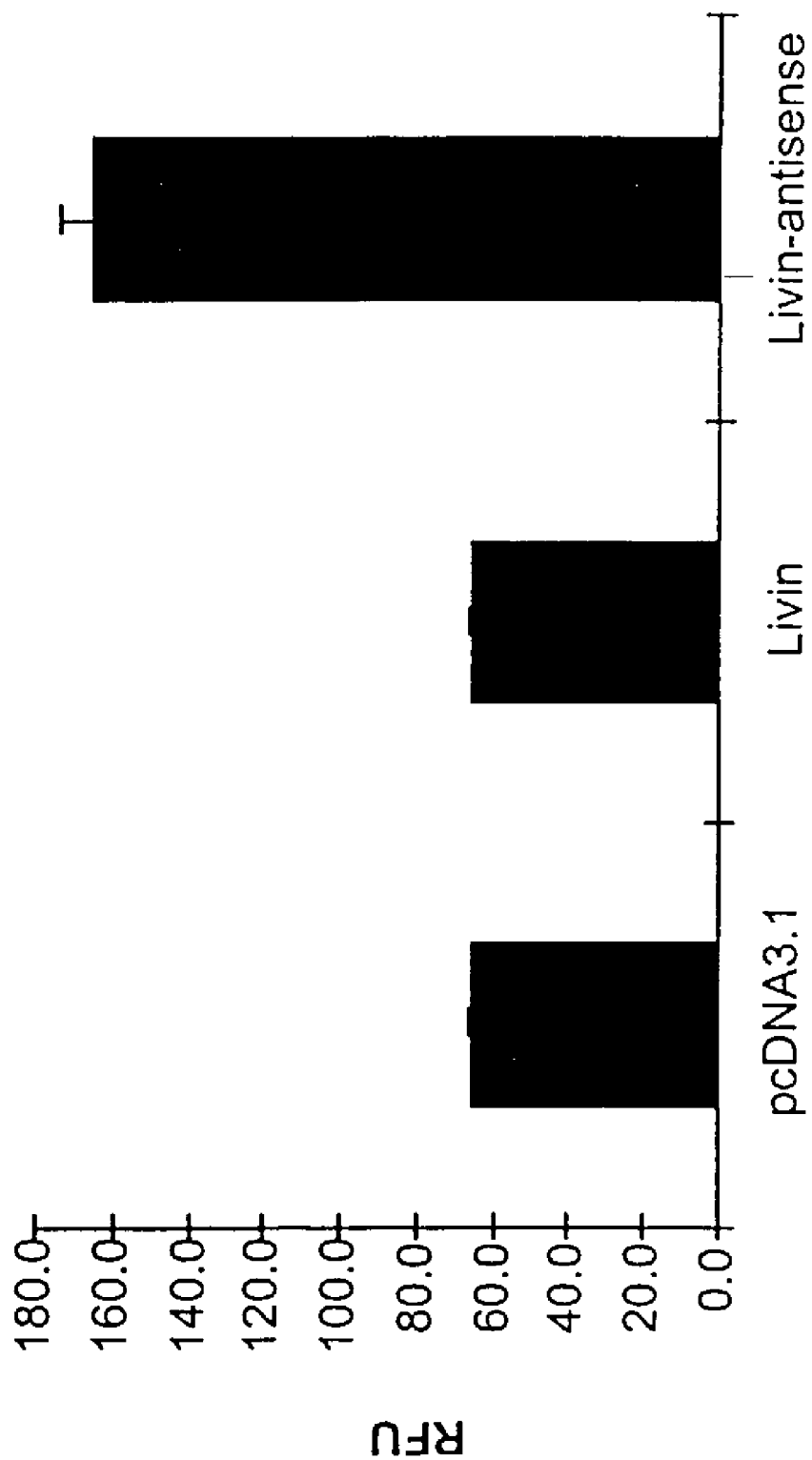

To extend these results, apoptosis was evaluated in more detail by measuring DNA fragmentation and caspase activation. DNA fragmentation was assessed using the TUNEL assay. Transfection of the antisense construct into G361 cells triggered an ~8% increase in TUNEL staining (FIG. 2B). Typically, the transfection efficiency in these cells was 15–20% suggesting that about half of the transfected cells were TUNEL-positive. To test whether this correlated with an increase in caspase activity, cytosolic extracts of the transfected cells were incubated with the fluorescent substrate, DEVD-AFC. Transfections with the antisense triggered nearly a 3-fold increase in DEVD-AFC cleavage (FIG. 2C). Presumably, this increase in caspase activity is a consequence of diminished livin-caspase interaction.

Example VI

Livin Inhibits Caspase Activity and Binds to Caspase-3, -7 and -9

Since other IAP family members have been shown to interact with caspases and abrogate their activity, we examined whether livin could function in a similar manner. The effect of livin on caspase activity was tested in HeLa cells treated with TNF-a. TNF-a-induced apoptosis involves a complex signaling response that includes activation of caspase-8 at the receptor level leading to activation of downstream caspases including caspase-3 and -7 (Green (1998) *Cell* 94:695–698). TNF-a also leads to the release of cytochrome c from the mitochondria resulting in the activation of caspase-9 and subsequently caspase-3. TNF-a also induces the NF-kB which can inhibit apoptosis but can be blocked using cycloheximide.

HeLa cells (2×10$^5$) transfected with livin, the anti-apoptotic gene bcl-x$_L$ (1 μg of pcDNA3.1/V5/His-TOPO-livin, pZeoSV2-Bcl-x$_L$, or empty pcDNA3.1 control. or empty vector) were subsequently treated with TNF-a and cycloheximide. Caspase activity was measured using the fluorescent substrate DEVD-AFC, used to specifically detect DEVD-cleaving caspases (caspase-3, -6, -7, -8, and -10). Treatment with TNF-a (1000 U/ml) and cycloheximide (30 μg/ml) for five hours for five hours led to ~7-fold increase in DEVD-AFC cleavage, demonstrating that livin inhibits TNF-a-triggered caspase activation.

However, cells transfected with livin exhibited reduced caspase activity by 15–20%, consistent with the transfection efficiency of these cells. Comparable levels of caspase inhibition were observed upon transfection with bcl-$x_L$. These results demonstrate the ability of livin to inhibit DEVD-like caspase activity.

Binding between livin and caspases was tested by incubating $^{35}$[S]-methionine-labeled livin with recombinant active caspase-3 and -7, immunoprecipitating with caspase specific antibodies, resolving on SDS-PAGE and visualising by autoradiography. Both caspase-3 and -7 interacted with livin, but not with the deletion mutant DC89 used as a negative control. Survivin, which was previously shown to interact with these caspases using whole cell lysates (Tamm et al., ibid), also bound to both caspases in this in vitro assay. Together, these results demonstrate direct interactions between survivin/livin and the activated form of the caspase-3 and -7. This interaction is likely to occur via the BIR domain, which has been shown to be sufficient for caspase binding with other IAP family members and confirmed here to be sufficient for livin as well.

In addition to binding caspases-3 and -7, XIAP, c-IAP1, and c-IAP2 have been shown to bind to the unprocessed form of caspase-9 and prevent its processing (Deveraux et al. ibid). Associations between livin or surivivin with caspase-9 was tested in HeLa cells transfected with these IAP family members. The cells were subsequently treated with TNF-a to evaluate interactions with activated caspase-9, or left untreated to examine the unprocessed form. Cell lysates were immunoprecipitated with antibodies against the epitope tags on livin (V5) and survivin (myc) and then probed by Western blot for caspase-9. In the absence of TNF-a, livin, but not survivin, immunoprecipitated with the unprocessed 45 kDa form of caspase-9. Upon stimulation with TNF-a, an increase in binding was observed between livin and the 35 kDa cleaved form of caspase-9. These data demonstrate an association between livin and the zymogen and cleaved forms of caspase-9, and illustrates a functional distinction between livin and survinin.

Associations with caspase-9 were shown using HeLa cells transiently transfected with either pcDNA3.1/V5/His-TOPO-livin or pcDNA3.1-myc-survivin and treated with TNF-a and cycloheximide. Cell lysates were prepared in RIPA buffer as described above and immunoprecipitated using either a monoclonal antibody against V5 (Invitrogen, Carlsbad, Calif.) followed by protein G sepharose or with a monoclonal antibody against myc conjugated to agarose (Santa Cruz Biotechnology, Santa Cruz, Calif.). Blots were probed with a monoclonal antibody against caspase-9 (PanVera Corporation, Madison, Wis.) and detected by ECL.

Fluorometric Caspase Activation Assays

Caspase activity was measured using the ApoAlert® caspase-3 fluorescent assay kit (Clontech, Palo Alto, Calif.). Cytosolic lysates were prepared from transiently transfected cells. Lysates were incubated with 50 µM of the fluorescent substrate 7-amino-4-trifluoromethyl coumarin (AFC) conjugated to the caspase cleavage site Asp-Glu-Val-Asp (DEVD) for 1 hr at 37° C. Hydrolyzed AFC was detected using a CytoFluor® 4000 fluorometer (PerSeptive Biosystems, Framingham, Mass.) with peak excitation/bandwidth at 360/40 nm and peak emission/bandwidth at 530/30 nm.

In vitro Binding Assay

In vitro binding reactions were performed by combining recombinant active caspase-3 or -7 (PharMingen, San Diego, Calif.) with $^{35}$[S]-methionine-labeled survivin or livin (wild-type and the three deletion mutants described herein), prepared using the TNT T7 reticulocyte lysate system (Promega Corp., Madison, Wis.). Samples were incubated with polyclonal antibodies against either caspase-3 or -7 (PharMingen, San Diego, Calif.) in 0.5 ml NETN buffer [20 mM Tris (pH 8.0), 100 mM NaCl, 1 mM EDTA, and 0.2% NP-40] for 1.5 hrs at 4° C. followed by protein G sepharose (Amersham Pharmacia Biotech, Piscataway N.J.) for 30 min. All samples were then washed three times in NETN buffer, boiled in Laemmli buffer, and resolved by 4–20% SDS-PAGE. Gels w ere fixed in 50% methanol, 10% acetic acid for 1 hour, dried, and then visualized using a Phosphorimager (Molecular Dynamics, Sunnyvale, Calif.).

Immunoprecipitations and Western Blotting

Endogenous livin protein was immunoprecipitated from G361 cells. Cell lysates were prepared in 1 ml of RIPA buffer [0.01 M sodium phosphate (pH 7.2), 150 mM NaCl, 2 mM EDTA, 50 mM NaF, 1% NP-40, 1% sodium deoxycholate, and 0.1% SDS] supplemented with a protease inhibitor cocktail tablet (Boehringer Mannheim, Indianapolis, Ind.). Samples were spun at 14,000 rpm for 30 min at 4° C. The soluble supernatants were either incubated with antibodies against livin (V5) or, as a control, with rabbit polyclonal antibodies against myc (Santa Cruz Biotechnology, Santa Cruz, Calif.) for 1.5 hrs at 4° C. followed by protein G sepharose for 30 min. The samples were washed three times in RIPA buffer, boiled in Laemmli buffer, and resolved by 4–20% SDS-PAGE. The gels were semi-dry blotted onto nitrocelluose and probed with the livin antibody. Immunocomplexes were detected by enhanced chemiluminescence (ECL) according to the manufacturer's specifications (Amersham Pharmacia Biotech, Piscataway, N.J.).

Example VIII

Detection of Sub-Cellular Localisation of Livin and Survivin by Immunofluorescence Differential subcellular localization of the IAP family members have implied distinct roles in apoptosis regulation (Vucic et al., ibid; Li et al., (1998) ibid). Staining for livin was performed using antibodies against the V5 epitope tag in transfected HeLa cells. The sub-cellular localizations of livin and survivin were assessed by indirect immunofluorescence from HeLa cells transfected with epitope-tagged expression constructs. HeLa cells ($2\times10^5$) were transfected with 1 µg of pcDNA3.1-myc-survivin, pcDNA3.1/V5/His-TOPO-livin, or pcDNA3.1/myc-His-livin DN154. Twenty-four hours post-transfection the cells were fixed with 2% paraformaldehyde and then permeabilized with 0.2% Triton X-100 in PBS. Coverslips were incubated with antibodies against the V5 or myc (Oncogene Research Products, Cambridge, Mass.) epitopes for 1 hr at 37° C. Staining was detected using a FITC-conjugated goat-anti-mouse antibody (Life Technologies, Grand Island, N.Y.) for 1 hr at 37° C. Cells were visualized by epifluorescence using an Olympus AX70 microscope equipped with a Kodak DCS 520 digital camera (Hitech Instruments, Inc., Edgemont, Pa.).

Livin was observed predominantly in a filamentous pattern throughout the cytoplasm and nucleus. Since survivin was shown to associate with microtubules (Li et al., (1998) ibid), we asked whether the pattern of livin localization resembles survivin. Transfected survivin was stained using antibodies against the myc epitope. Like livin, survivin was found in filamentous pattern throughout the cell.

To determine the critical motifs required for the localization of livin, HeLa cells were transfected with the deletion mutants DC86, 86–154, and DN154 each containing a myc epitope tag used for staining. The truncated proteins DC86 and 86–154 produced aberrant diffuse staining. However, DN154, which contains the ~35 amino acid RING domain, was found in the same filamentous pattern as the wild-type protein. These results suggest that the COOH-terminal region of livin, and perhaps more specifically the RING domain, provides a sufficient signal for its proper subcellular distribution. Interestingly, other IAP family members that have RING domains do not localize in the filamentous pattern seen here (Vucic et al., ibid). This disparity suggests that the function of the RING domain, like the BIR domain, is not absolutely conserved but rather may depend on either the particular IAP and/or cell type in which it is expressed.

Interactions between survivin and microtubules at mitotic spindle have implicated a role for survivin in protecting cells from apoptosis during mitosis (Li et al., (1999) ibid; Li et al., (1998) ibid). Perhaps, the common localization between survivin and livin signifies similar roles with respect to inhibition of specific substrates from caspase cleavage. Interestingly, while the coiled-coil domain mediates the cytoskeletal interactions in survivin (Li et al., (1998) ibid), it appears that in livin, the RING domain mediates a similar interaction. The functions of RING domains have been largely enigmatic, although they are often associated with mediating multi-protein complexes and in some cases co-precipitate with cytoskeletal proteins (Suarin et al., (1996) TIBS 21:208–214).

Taking the functional and localization studies of livin together, one can propose a modular model whereby the BIR domain mediates its anti-apoptotic activity and interaction with caspases, while the RING domain provides proper cellular localization. In the case of survivin, removal of the coiled-coil domain inhibited microtubule interactions as well as suppression of Taxol-mediated apoptosis implying that the survivin-microtubule interaction is important for survivin's anti-apoptotic activity (Li et al., (1998) ibid). In contrast, the BIR domain of livin is sufficient for apoptosis yet does not localize in a filamentous pattern indicative of microtubule binding. While this disparity may simply reflect differences in the mechanism of apoptotic stimulus, it is possible that it signifies important differences in the mechanism of the two proteins.

In view of the localisation effect of the RING domain, this domain may be used to target heterologous sequences or molecules (toxins etc) for therapuetic or other uses.

The invention claimed is:

1. An isolated and/or purified polynucleotide molecule comprising a nucleic acid sequence which encodes a polypeptide comprising the amino acid sequence of SEQ ID NO: 3.

2. An expression vector comprising the polynucleotide of claim 1.

3. A cultured host cell transformed or transfected with the expression vector of claim 2.

4. An isolated polynucleotide comprising the nucleotide sequence of SEQ ID NO: 1 or SEQ ID NO: 2, or a nucleotide sequence fully complementary thereto.

5. A method of producing a polypeptide comprising culturing a host cell transformed or transfected with an expression vector comprising a polynucleotide which encodes the polypeptide, wherein the polypeptide comprises the amino acid sequence of SEQ ID NO: 3.

6. The method of claim 5, additionally comprising purifying the polypeptide from the cells or the culture medium.

7. An oligomer which is the complete complement to the sequence selected from the group consisting of positions 194–206; 195–207; 196–208; 197–209; 198–210; 199–211, 200–212; 201–213; 202–214; 203–215; 204–216; 205–217; 206–218; 207–219; 208–220; 209–221; 210–222; 211–223; 212–224; 213–225; 214–226; 215–227; 216–228; 220–232; 225–237; 230–242; 240–252; 250–262; 270–282; 520–532; 525–537; 529–541; 530–542; 555–567; 560–572; 570–582; 590–602; and 600–612 of SEQ ID NO: 1.

* * * * *

UNITED STATES PATENT AND TRADEMARK OFFICE
CERTIFICATE OF CORRECTION

PATENT NO. : 7,183,396 B2  Page 1 of 1
APPLICATION NO. : 10/244586
DATED : February 27, 2007
INVENTOR(S) : Gomes et al.

It is certified that error appears in the above-identified patent and that said Letters Patent is hereby corrected as shown below:

<u>In the title</u>:

Item (54); please change "LINVIN" to correctly read --LIVIN--.

Signed and Sealed this

Twenty-ninth Day of May, 2007

JON W. DUDAS
*Director of the United States Patent and Trademark Office*

SEQUENCE LISTING

<160> NUMBER OF SEQ ID NOS: 12

<210> SEQ ID NO 1
<211> LENGTH: 1376
<212> TYPE: DNA
<213> ORGANISM: Homo sapiens

<400> SEQUENCE: 1

```
taccggtccg gaattcccgg gtcgacccac gcgtccgccc tgggatactc ccctcccagg      60
gtgtctggtg gcaggcctgt gcctatccct gctgtcccca gggtgggccc cgggggtcag     120
gagctccaga agggccagct gggcatattc tgagattggc catcagcccc catttctgct     180
gcaaacctgg tcagagccag tgttccctcc atgggaccta aagacagtgc caagtgcctg     240
caccgtggac cacagccgag ccactgggca gccggtgatg gtcccacgca ggagcgctgt     300 ggacccgct ctctgggcag ccctgtccta ggcctggaca cctgcagagc ctgggaccac     360
gtggatgggc agatcctggg ccagctgcgg ccctgacag aggaggaaga ggaggagggc     420
gccggggcca ccttgtccag ggggcctgcc ttccccggca tgggctctga ggagttgcgt     480
ctggcctcct tctatgactg gccgctgact gctgaggtgc cacccgagct gctggctgct     540
gccggcttct tccacacagg ccatcaggac aaggtgaggt gcttcttctg ctatgggggc     600
ctgcagagct ggaagcgcgg ggacgacccc tggacggagc atgccaagtg gttccccagc     660
tgtcagttcc tgctccggtc aaaaggaaga gactttgtcc acagtgtgca ggagactcac     720
tcccagctgc tgggctcctg ggacccgtgg gaagaaccgg aagacgcagc ccctgtggcc     780
ccctccgtcc ctgcctctgg gtaccctgag ctgcccacac ccaggagaga ggtccagtct     840
gaaagtgccc aggagccagg agccagggat gtggaggcgc agctgcggcg gctgcaggag     900
gagaggacgt gcaaggtgtg cctggaccgc gccgtgtcca tcgtctttgt gccgtgcggc     960
cacctggtct gtgctgagtg tgcccccggc ctgcagctgt gcccatctg cagagccccc    1020 gtccgcagcc gcgtgcgcac cttcctgtcc taggccaggt gccatggccg gccaggtggg    1080
ctgcagagtg ggctccctgc ccctctctgc ctgttctgga ctgtgttctg ggcctgctga    1140
```

```
ggatggcaga gctggtgtcc atccagcact gaccagccct gattccccga ccaccgccca    1200
gggtggagaa ggaggcccct tgcttggcgtg ggggatggct taactgtacc tgtttggatg    1260
cttctgaata gaaataaagt gggttttccc tggaggtaaa aaaaaaaaaa aaagggcggc    1320
cgctctagag gatccctcga ggggcccaag cttacgcgtg catgcgacgt catagt       1376

<210> SEQ ID NO 2
<211> LENGTH: 843
<212> TYPE: DNA
<213> ORGANISM: Homo sapiens

<400> SEQUENCE: 2
atgggaccta agacagtgc caagtgcctg caccgtggac cacagccgag ccactgggca     60
gccggtgatg gtcccacgca ggagcgctgt ggaccccgct ctctgggcag ccctgtccta   120
ggcctggaca cctgcagagc ctgggaccac gtggatgggc agatcctggg ccagctgcgg   180
cccctgacag aggaggaaga ggaggagggc gccggggcca ccttgtccag ggggcctgcc   240
ttccccggca tgggctctga ggagttgcgt ctggcctcct tctatgactg gccgctgact   300
gctgaggtgc cacccgagct gctggctgct gccggcttct tccacacagg ccatcaggac   360
aaggtgaggt gcttcttctg ctatggggc ctgcagagct ggaagcgcgg ggacgacccc    420
tggacggagc atgccaagtg gttccccagc tgtcagttcc tgctccggtc aaaaggaaga   480
gactttgtcc acagtgtgca ggagactcac tcccagctgc tgggctcctg ggacccgtgg   540
gaagaaccgg aagacgcagc ccctgtggcc cctccgtcc tgcctctggg taccctgag    600 ctgcccacac ccaggagaga ggtccagtct gaaagtgccc aggagccagg agccagggat   660
gtggaggcgc agctgcggcg gctgcaggag gagaggacgt gcaaggtgtg cctggaccgc   720
gccgtgtcca tcgtctttgt gccgtgcggc cacctggtct gtgctgagtg tgccccggc    780 ctgcagctgt gccccatctg cagagccccc gtccgcagcc gcgtgcgcac cttcctgtcc   840
tag                                                                 843

<210> SEQ ID NO 3
<211> LENGTH: 280
<212> TYPE: PRT
<213> ORGANISM: Homo sapiens

<400> SEQUENCE: 3

Met Gly Pro Lys Asp Ser Ala Lys Cys Leu His Arg Gly Pro Gln Pro
  1               5                  10                  15

Ser His Trp Ala Ala Gly Asp Gly Pro Thr Gln Glu Arg Cys Gly Pro
             20                  25                  30

Arg Ser Leu Gly Ser Pro Val Leu Gly Leu Asp Thr Cys Arg Ala Trp
         35                  40                  45

Asp His Val Asp Gly Gln Ile Leu Gly Gln Leu Arg Pro Leu Thr Glu
     50                  55                  60

Glu Glu Glu Glu Glu Gly Ala Gly Ala Thr Leu Ser Arg Gly Pro Ala
 65                  70                  75                  80

Phe Pro Gly Met Gly Ser Glu Glu Leu Arg Leu Ala Ser Phe Tyr Asp
                 85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
```

```
             130                 135                 140
Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
                195                 200                 205

Gln Ser Glu Ser Ala Gln Glu Pro Gly Ala Arg Asp Val Glu Ala Gln
    210                 215                 220

Leu Arg Arg Leu Gln Glu Glu Arg Thr Cys Lys Val Cys Leu Asp Arg
225                 230                 235                 240

Ala Val Ser Ile Val Phe Val Pro Cys Gly His Leu Val Cys Ala Glu
                245                 250                 255

Cys Ala Pro Gly Leu Gln Leu Cys Pro Ile Cys Arg Ala Pro Val Arg
            260                 265                 270

Ser Arg Val Arg Thr Phe Leu Ser
        275                 280

<210> SEQ ID NO 4
<211> LENGTH: 21
<212> TYPE: DNA
<213> ORGANISM: Homo sapiens

<400> SEQUENCE: 4
ccttctatga ctggccgctg a                                           21

<210> SEQ ID NO 5
<211> LENGTH: 32
<212> TYPE: DNA
<213> ORGANISM: Homo sapiens

<400> SEQUENCE: 5
ggccggaagc ttatgctccg gtcaaaagga ag                               32

<210> SEQ ID NO 6
<211> LENGTH: 32
<212> TYPE: DNA
<213> ORGANISM: Homo sapiens

<400> SEQUENCE: 6
gcgcgcgggc ccccggacag gaagggcgc ac                                32

<210> SEQ ID NO 7
<211> LENGTH: 30
<212> TYPE: DNA
<213> ORGANISM: Homo sapiens

<400> SEQUENCE: 7
ggccggaagc ttatgggacc taaagacagt                                  30

<210> SEQ ID NO 8
<211> LENGTH: 32
<212> TYPE: DNA
<213> ORGANISM: Homo sapiens

<400> SEQUENCE: 8
gcgcgcgggc cccagagcc catgccgggg aa                                32
```

```
<210> SEQ ID NO 9
<211> LENGTH: 31
<212> TYPE: DNA
<213> ORGANISM: Homo sapiens

<400> SEQUENCE: 9
ggccggtacc atggaggagt tgcgtctggc c                              31

<210> SEQ ID NO 10
<211> LENGTH: 32
<212> TYPE: DNA
<213> ORGANISM: Homo sapiens

<400> SEQUENCE: 10
gcgcgcgggc cccccaggaa ctgacagctg gg                             32

<210> SEQ ID NO 11
<211> LENGTH: 21
<212> TYPE: PRT
<213> ORGANISM: Homo sapiens

<400> SEQUENCE: 11

Leu Pro Thr Pro Arg Arg Glu Val Gln Ser Glu Ser Ala Gln Glu Pro
 1               5                  10                  15

Gly Ala Arg Asp Val
            20

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      caspase cleavage site

<400> SEQUENCE: 12

Asp Glu Val Asp
 1
```